United States Patent [19]
Ash et al.

[11] Patent Number: 6,004,452
[45] Date of Patent: Dec. 21, 1999

[54] PROCESS FOR CONVERTING HYDROCARBON FEED TO HIGH PURITY BENZENE AND HIGH PURITY PARAXYLENE

[75] Inventors: Gary A Ash, Kingwood, Tex.; Nhu Q Dao, Richmond, Calif.; Arnold J Gloyn, Walnut Creek, Calif.; N J Haritatos, El Cerrito, Calif.; Paul I Hodgen, Sugar Land, Tex.; Stuart R MacPherson, Mobile, Ala.; Scott Gordon Morrison, Petaluma; Gerald J Nacamuli, Mill Valley, both of Calif.; Paul M Spindler, Kingwood, Tex.; Bruce J Thom, Concord, Calif.; Eric P Weber, Kingwood, Tex.; Richard Wolpert, Berkeley, Calif.

[73] Assignee: Chevron Chemical Company LLC, San Francisco, Calif.

[21] Appl. No.: 08/968,462

[22] Filed: Nov. 14, 1997

[51] Int. Cl.$^6$ .................................................. C10G 51/06
[52] U.S. Cl. ............................ 208/80; 208/79; 208/134; 208/141; 585/300; 585/302; 585/805; 585/812
[58] Field of Search ................................ 208/79, 80, 134, 208/141; 585/300, 302, 805, 812

[56] References Cited

U.S. PATENT DOCUMENTS

| | | | |
|---|---|---|---|
| Re. 33,323 | 9/1990 | Roarty et al. | 208/79 |
| 2,653,175 | 9/1953 | Davis | 585/302 |
| 2,867,576 | 1/1959 | Honeycutt | 208/65 |
| 3,216,789 | 11/1965 | Breck et al. | 23/113 |
| 3,280,022 | 10/1966 | Engel et al. | 208/64 |
| 3,753,891 | 8/1973 | Graven et al. | 208/62 |
| 3,761,392 | 9/1973 | Pollock | 208/93 |
| 3,928,174 | 12/1975 | Bonacci et al. | 208/80 |
| 3,957,621 | 5/1976 | Bonacci et al. | 208/60 |
| 4,016,219 | 4/1977 | Kaeding | 260/672 T |
| 4,052,476 | 10/1977 | Morrison | 260/672 T |
| 4,067,919 | 1/1978 | Butter | 260/668 D |
| 4,097,543 | 6/1978 | Haag et al. | 260/672 T |
| 4,104,320 | 8/1978 | Bernard et al. | 260/673.5 |
| 4,160,788 | 7/1979 | Young | 585/475 |
| 4,167,472 | 9/1979 | Dick et al. | 208/80 |
| 4,190,520 | 2/1980 | Gewartowski | 208/95 |
| 4,203,826 | 5/1980 | Mayes | 208/64 |
| 4,401,554 | 8/1983 | Choi et al. | 208/64 |
| 4,434,311 | 2/1984 | Buss et al. | 585/444 |
| 4,448,891 | 5/1984 | Cohen | 502/74 |
| 4,594,145 | 6/1986 | Roarty | 208/79 |
| 4,608,356 | 8/1986 | Buss et al. | 502/66 |
| 4,634,518 | 1/1987 | Buss et al. | 208/138 |
| 4,720,602 | 1/1988 | Chu | 585/407 |
| 4,721,694 | 1/1988 | Buss et al. | 502/66 |
| 4,830,732 | 5/1989 | Mohr et al. | 208/138 |
| 4,891,463 | 1/1990 | Chu | 585/415 |
| 4,897,177 | 1/1990 | Nadler | 208/79 |
| 4,899,011 | 2/1990 | Chu et al. | 585/481 |
| 4,962,257 | 10/1990 | Absil et al. | 585/475 |
| 4,987,109 | 1/1991 | Kao et al. | 502/66 |
| 5,106,484 | 4/1992 | Nadler et al. | 208/41 |
| 5,284,992 | 2/1994 | Hotier et al. | 585/805 |
| 5,329,060 | 7/1994 | Swift | 585/805 |
| 5,401,365 | 3/1995 | Chen et al. | 203/32 |
| 5,401,366 | 3/1995 | Berg | 203/57 |
| 5,401,476 | 3/1995 | Hotier et al. | 422/222 |
| 5,472,593 | 12/1995 | Gosling et al. | 208/65 |
| 5,573,645 | 11/1996 | Pickering, Jr. | 203/25 |

FOREIGN PATENT DOCUMENTS

| | | |
|---|---|---|
| 335540B1 | 8/1994 | European Pat. Off. . |
| WO96/20907 | 7/1996 | WIPO . |
| WO96/20908 | 7/1996 | WIPO . |
| WO96/22262 | 7/1996 | WIPO . |

OTHER PUBLICATIONS

Hiromichi Arai, et al., The Influence of Platinum Particle Size on the Activity and Selectivity of Reforming Catalysts, Stud. In_Sci & Catal., vol. 7, 1446–1447 (1981).

Cvedana Besoukhanova, et al., Platinum–Zeolite Interactions in Alkaline L Zeolites, J. Chem. Soc., Faraday Trans. 1, 1981, 77, 1595–1604.

W.J. Reagan, et al., Studies of the Thermal Decomposition and Catalytic Properties of Some Platinum and Palladium Ammine Zeolines, Journal of Catalysts 69, 89–100 (1981), Academic Press, Inc., USA.

J.A. Johnson, et al., Sorbex A Commercially Proven Route to High Purity Chemicals, Proceedings of The Royal Swedish Academy of Engineering Sciences Symposium, Separation Technology for Fine Chemicals, Stockholm, Sweden, Mar. 3, 1987.

R.E. Prada, et al., Parex Developments for Increased Efficiency, 1992 UOP.

J.D. Swift, et al., New Options for Aromatics Production; Mar. 1995 DeWitt Petrochemical Review.

*Primary Examiner*—Walter D. Griffin
*Assistant Examiner*—Thuan D. Dang
*Attorney, Agent, or Firm*—Tobor, Goldstein & Healey, L.L.P.

[57] ABSTRACT

A process is provided for producing high purity benzene and high purity paraxylene from a hydrocarbon feed. In one aspect, the process comprises: (a) reforming a hydrocarbon feed using either a monofunctional catalyst or a bifunctional catalyst to provide one or more reformate streams; (b) fractionating the reformate stream to provide a toluene stream, a benzene stream, and a xylene stream; (c) subjecting the toluene stream to disproportionation; (d) purifying the benzene stream by extraction followed by distillation to provide a high purity benzene product; and (e) purifying the xylene stream by simulated moving bed countercurrent adsorption followed by crystallization to provide a high purity paraxylene product.

10 Claims, 10 Drawing Sheets

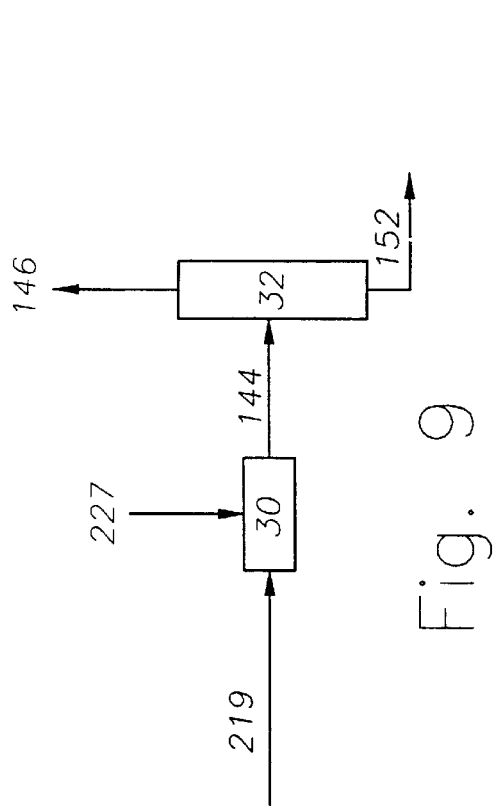
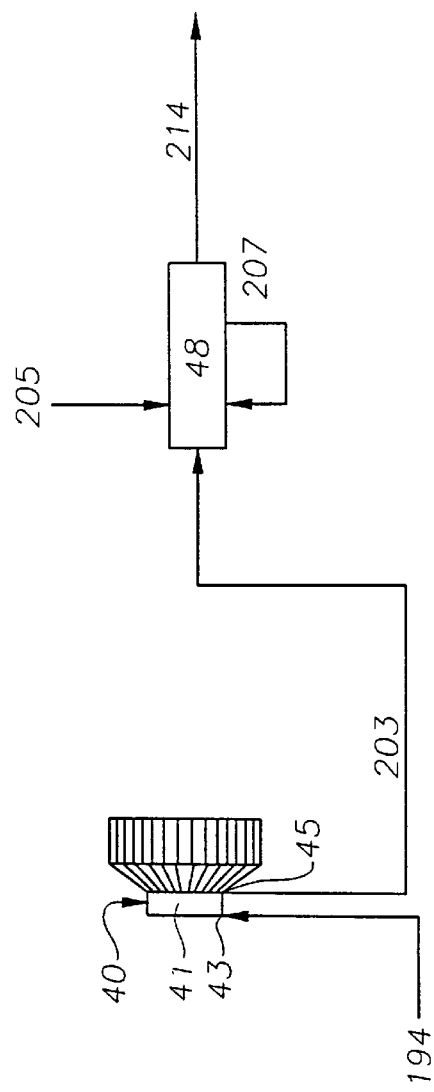

PROCESS FOR CONVERTING HYDROCARBON FEED TO HIGH PURITY BENZENE AND HIGH PURITY PARAXYLENE

FIELD OF THE INVENTION

The present invention relates broadly to methods for producing benzene and paraxylene. In another broad aspect, the invention is directed to a continuous benzene-toluene-xylene process ("BTX" process), wherein extremely high purity benzene (e.g., as high as 99.984 wt %) and extremely high purity paraxylene (e.g., as high as 99.9 wt %) are continuously produced from a wide boiling range naphtha feed (raw naphtha) having a variable composition.

BACKGROUND OF THE INVENTION

Over the years, the producers and users of benzene and paraxylene have periodically modified product specifications to require increased purity. Customers now desire extremely high purity products. While these ultra-high purity products can be reliably made on a small scale, it is much more difficult to consistently achieve such purity on a commercial scale. The problem is magnified when using naphtha feedstocks with variable or fluctuating compositions.

Benzene and paraxylene are typically produced from petroleum naphtha by a variety of reforming operations, also referred to herein as "aromatizing" operations. Raw naphtha is typically highly paraffinic in nature, but may contain significant amounts of naphthenes and minor amounts of aromatics or olefins, or both. Often, the naphtha feed is hydrodesulfurized prior to reforming to reduce catalyst poisoning. The objective in reforming is to produce a slate of aromatics, for example, from C6 to C10 aromatics, which can be subsequently further processed to produce the desired aromatics products such as benzene and paraxylene. Reforming includes dehydrogenation, isomerization and hydrocracking reactions. Dehydrogenation reactions typically include dehydroisomerization of alkylcyclopentanes to aromatics, dehydrogenation of paraffins to olefins, dehydrogenation of cyclohexanes to aromatics, and dehydrocyclization of paraffins and olefins to aromatics. Isomerization reactions include isomerization of n-paraffins to isoparaffins, hydroisomerization of olefins to isoparaffins and isomerization of substituted aromatics. Hydrocracking reactions include hydrocracking of paraffins and hydrodesulfurization if any sulfur compounds remain in the feedstock. Hydrocracking reactions are considered undesirable when they result in the formation of low carbon number gaseous products or light ends.

Numerous patents discuss the general concept of splitting a naphtha feed stream into a light fraction and a heavy fraction, then reforming each fraction separately. The following split feed patents are hereby incorporated by reference, to the extent they are not inconsistent with this invention: U.S. Pat. No. 4,897,177; U.S. Pat. Nos. 5,106, 484; Re 33,323; 3,957,621; 2,867,576; 2,944,959; 3,172, 841; 3,409,540; 4,167,472; 4,358,364; 3,753,891; 4,645, 586; 3,280,022; 2,867,576; 3,753,891; 4,401,554; 4,203, 826; 3,635,815; 3,499,945; 2,653,175.

Reforming is generally done in the presence of a catalyst. Numerous patents, including some of those listed above, disclose different types of commercially available catalysts that may be used to reform naphtha. Catalysts are also disclosed in Pat. Nos. 4,347,394 and 4,104,320, which are hereby incorporated by reference to the extent they are not inconsistent with the present invention. Often, two different types of catalyst systems are used to produce aromatics in split-feed reforming. The '177 patent discusses the use of non-acidic "monofunctional" catalysts, for reforming light fractions, and acidic "bifunctional" catalysts for reforming heavy fractions.

Bifunctional catalysts have metal sites and strong acid sites. In certain bifunctional catalysts, a metal hydrogenation-dehydrogenation component is dispersed on the surface of a porous inorganic oxide support such as alumina oxide. Additional metallic components, known as promoters, may be added to the platinum metal sites to provide increased activity or selectivity or both. Examples of promoters include iridium, rhenium, tin, and the like. In contrast, monofunctional catalysts are "non-acidic," and have large pore zeolites as supports rather than inorganic oxides such as alumina. Suitable monofunctional catalysts include non-acidic carriers such as a zeolite L, and at least one noble metal of Group VIII. "Nonacidic" or "monofunctional" reforming catalysts are characterized by a substantial absence of accessible acidic sites. The substantial absence of accessible acidic sites can be inferred from the reforming reaction products or determined by various analytical techniques well known in the art. For example, certain bands in O—H stretching region of infrared spectrum of the catalyst can be used to measure the number of acid sites that are present. For purposes of this invention, nonacidic catalysts will include any zeolite based catalyst having a silica/aluminum ratio greater than 500 or having no more than 5.0%, and preferably less than 1.0%, of its exchangeable cation sites occupied by protons. A nonacidic reforming catalyst typically comprises platinum on a substantially non-acidic support. A substantially non-acidic support material has an $\alpha$ less than about 0.1, where $\alpha$ refers to the relative n-hexane cracking activity of the support compared to a standard silica/alumina catalyst as determined in the well known Alpha Test, which is described in U.S. Pat. No. 3,354,078 and in the journal "Catalysis," Vol. 4, p. 527 (1965); Vol. 6, p. 278 (1966); and Vol. 61, p. 395 (1980).

In one aspect, the present invention relates to an improved split-feed method of making high purity benzene and high purity paraxylene using a dual catalyst system. While the prior art discloses monofunctional and bifunctional catalysts and split feed processes in general, it fails to disclose or suggest one or more key aspects or advantages of the present invention. For example, the '177 patent identifies several possible light and heavy fractions, including a light fraction of C6–C7. (Col. 4, ln 21.) It also implies that the heavy fraction may include C8+'s. (Col. 4, lns 13–16.) However, the patent states that the preferred light fraction is C6–C8, and thus directs one away from the C7–/C8+ split of the present invention. Moreover, it discloses nothing about the removal of heavy ends from the raw naphtha, nor does it suggest the surprisingly high RON of the present invention, nor does it suggest the cut point adjustment feature of the present invention.

The '323 patent discloses a split feed process. But that process is based on a C6– light fraction and a C7+ heavy fraction. While the light fraction is said to have 10% or more C7+'s, there is no suggestion to provide a C8+ heavy fraction or to restrict C7–'s in the heavy fraction. In fact, the '323 patent states that the C7+ fraction contains "greater than 90%, preferably at least 95%" of C7+'s. (Col. 3, lns 62–64.) Example 1 discloses a heavy fraction containing 91.9% C7 to C9 hydrocarbons. (Col. 7, ln 2.) The catalysts used to reform the heavy fraction are said to be "efficient in converting C7+ hydrocarbons," so that the '323 patent does not at all provide any motivation to provide a C7– light fraction and a C8+ heavy fraction. (Col. 5, lns 40–42.) Likewise, no other features of this invention are disclosed.

A publication by Swift and Moser, entitled "New Options for Aromatics Production," published in 1995, refers to several processes for making benzene and paraxylene. One process involves splitting a full-range naphtha into "light and heavy cuts" and directing the light fraction to the "RZ Platforming" unit and the heavy fraction to the "CCR Platforming" unit (See p. 7 and FIG. 6.) However, there is no disclosure of any particular composition of the heavy fraction that is treated in the CCR unit, much less any suggestion to restrict the amount of C7–'s in the heavy fraction, nor is there any suggestion of other aspects of this invention, including the unusually high RON of the heavy fraction reformate. Furthermore, that articles does not disclose any means for recovering a high purity benzene product, nor a method for accomodating highly fluctuating naphtha feedstock.

The '554 patent discloses a split feed process, but discloses a very broad cut point range of between 200° F. to 350° F. The cut point is said to be preferably the mid-point boiling range of the naphtha. That patent states that the heavy fraction contacts the reforming catalyst for a longer period than the light fraction, so that "for a given severity the degree of reforming reaction for the heavy fraction is much higher than the light fraction." (Col. 5, lns 8–11.) However, in addition to not disclosing or suggesting the C7/C8 split feed aspect of this invention, that patent does not disclose the surprisingly high octane number of this invention. For example, the RON's disclosed are only 96 and 98. (See col. 6, lns 42–43 and Table 3.) Moreover, there is no suggestion to remove light or heavy ends, nor is there any suggestion to adjust the cut point based on benzene or paraxylene limit points.

The '621 patent discusses distillation of a reformate feed stream to provide light and heavy reformate product fractions. However, the light reformate product fraction (containing paraffins and some benzene) is removed as overhead and is not processed any further, e.g., to provide a high purity benzene product (Col. 4, lns 65–68; see FIG. 1, line 12.) Also, the feed stream being subjected to "splitting" is itself a reformate, and already contains a high concentration of aromatics. (Col. 4, lns 57–61.) That patent does not disclose splitting of raw naphtha feed into light and heavy fractions. Example 1 in the patent refers to production at a severity to produce C5+ reformate having 103 RON. Significantly, however, the charge used to produce that reformate is itself the "heavy end of a reformate." (Col. 14, ln 3.) Moreover, the naphtha feed used to produce that reformate feed is C6– naphtha. (Col. 14, ln 4.) Thus, the patent discloses neither C7–/C8+ splitting nor removal of light and heavy ends prior to splitting. Finally, the patent does not suggest adjusting the cut point based on benzene or paraxylene limit points.

The '891 patent involves a split feed process, where naphtha is separated into a light fraction and a heavy fraction. This patent states that the light fraction is "subjected generally to less severe reforming conditions than a higher boiling fraction." The light and heavy fractions are defined by various "cut points," but a cut point of about 200° F. or 240° F. is said to be preferred, "since it is intended to concentrate substantially all C6 hydrocarbons and a substantial portion, if not a major portion, of C7 hydrocarbons into the light naphtha fraction." (Col. 2, lns 64–67.) The heavy fraction is said to be that portion boiling below about 240° or 260° F. (Col. 5, lns 19–21.) A preferred cut point is 250° F. (Col. 14, ln 72.) The key features of the present invention, however, are not suggested. For example, in the '891 patent, a single type of catalyst is used in treating the split stream.

The '022 patent discloses splitting the naptha feed, but it also states that the C7's are combined with the heavy reformer feed. Moreover, a "typical operation," shown in a Table in columns 5 and 6, shows that the recycle stream combined with the feed to the heavy fraction reformer has 62.8% isoheptanes and 15.7% normal heptane. Furthermore, even after C5–'s are removed, the heavy fraction reformate (motor fuel 51) has an RON of only 96.5. Thus, that patent does not disclose or suggest the present invention.

As discussed below, one important aspect of the present invention is formation of a heavy fraction reformate having a surprisingly high RON, preferably 104 or above and more preferably 108 or above. As used herein, the "RON" of a material shall mean its research octane number as measured by ASTM D2699-95a. It is known that RON generally reflects the aromatics concentration, and is often used as a measurement of reformer severity. It is understood by persons skilled in the art that the RON can be boosted by manipulating operating conditions, e.g., by adjusting the temperature and/or pressure during reforming. This idea is discussed in the '826 patent. However, as acknowledged in that patent it is also known that increasing severity often leads to undesirable secondary reactions such as hydrocracking and coking, which reduce aromatics yield. In paraxylene production, such secondary reactions tend to reduce the yield of xylene precursors. Thus, typical reforming or aromatizing operations for making benzene and paraxylene products are conducted under moderately severe conditions, producing reformate with an RON of about 100, or perhaps slightly higher. Reformates as high as 103 are sometimes produced, as disclosed in the '177 patent. However, none of the references discloses boosting the RON to 104 or above or even 108 and above.

A frequent problem encountered with using petroleum naphtha as a feedstock is the unpredictable nature of the feed stream composition. The problem arises when the naphtha feed comes from more than one source depending on cost and availability. In such a situation, the petroleum naphtha feed does not have necessarily a set or predictable composition. This unpredictability is especially true of a "full boiling range naphtha," that is, naphtha hydrocarbon material boiling over one of several ranges. For example, one naphtha may boil over a range from about 104° C. to about 176° C. Another naphtha may boil over a range of from about 32° C. to about 204° C. Certain raw naphthas have a high proportion of heavy ends, such as C8's through C10's. Others have a high proportion of light ends, such as C6's and C7's. The present invention offers a method for continuously producing a high purity benzene and a high purity paraxylene while accomodating such fluctuations in naphtha feedstock composition.

Another aspect of the invention involves disproportionation of toluene, in combination with one or more of the other steps referenced above. It is known that disproportionation of toluene produces benzene and xylene. Disproportionation may be accomplished in a variety of ways. For example, the '177 patent discloses disproportionation using molecular sieve catalysts. However, in the '177 patent, and in other processes, the toluene stream is extracted before being subjected to disproportionation. Extraction removes non-aromatics that have boiling points close to toluene and are therefore difficult to remove by distillation. Toluene disproportionation is discussed in various patents, including U.S. Pat. Nos. 3,957,621; 4,052,476; 4,016,219; 4,097,543; 4,962,257; and 4,160,788. While the '621 patent refers to disproportionation of unextracted toluene, the stream containing the toluene that is treated to disproportionation is obtained from a reformate which is itself formed from a "heavy reformate" feedstock having large quantities of ethyl benzene, xylenes, and C9+ aromatics. Thus, the '621 patent fails to disclose or suggest the present invention, in which a C7– naphtha feed (light fraction) is reformed to provide a reformate rich in benzene and toluene, and where the reformate is subjected to disproportionation without further reforming, preferably after removal of benzene and xylenes.

Another aspect of this invention involves production of benzene, to surprisingly high levels of purity, e.g., up to 99.989 wt % benzene or even higher. Benzene is typically purified by aromatics extraction followed by distillation. For example, in the '177 patent, Sulfolane is used to purify a mixed aromatics stream, which is then subjected to distillation. However, there is no suggestion to clay treat or selectively hydrogenate the benzene in order to obtain a high purity product Surprisingly, with the present invention, a benzene product is obtained having a purity of about 99.989 wt % benzene or more. Surprisingly, this purity exceeds even the ASTM Refined Benzene-545 standard. Moreover, the benzene product of this invention preferably has a toluene concentration of about 40 ppm by weight or less and a non-aromatics concentration of about 70 ppm by weight or less.

Finally, another aspect of this invention is simultaneous production of high purity paraxylene from the same naphtha feedstock, e.g., a product that is up to about 99.9 wt %, or even higher, pure paraxylene. Various methods and techniques are known for producing paraxylene. Simulated moving bed liquid chromatography and fractional crystallization are often used to separate paraxylene from other xylene isomers and ethylbenzene. Other methods are disclosed in the '621 patent (col. 2, lns 23–32) and in U.S. Pat. Nos. 5,401,476, which are hereby incorporated herein by reference. Still other methods are disclosed by McPherson, in PCT Publication No. WO 96/22262, entitled "Process for Production of Paraxylene Comprising a High Temperature Crystallization With at Least One Stage and a Partial Melting of the Crystals," having corresponding U.S. application Ser. No. 08/875,278, which is hereby incorporated by reference. However, in many of these processes, the purity of the paraxylene product depends primarily on the composition of the feedstock, which usually includes a range of mixed xylenes, such as meta-xylene, ortho-xylene and para-xylene. Moreover, such processes are directed to paraxylene production, and do not involve simultaneous production of high purity benzene. Accordingly, the present invention offers an improvement to these processes.

SUMMARY OF THE INVENTION

In a broad aspect, this invention is directed to an improved process for simultaneously making high purity benzene and high purity paraxylene from a naphtha feedstock. Broadly, the process includes the steps of providing first and second naphtha fractions; reforming the first and second naphtha fractions in the presence of first and second catalysts to provide first and second reformates, the first reformate being rich in benzene and toluene, the second reformate being rich in mixed xylenes. A first benzene-rich stream is removed from the first reformate. The first benzene-rich stream is separated into a light fraction and a heavy fraction, and high purity benzene is recovered from the light fraction. Simultaneously, a first xylene-rich stream should be removed from the second reformate stream. A benzene-rich fraction is preferably removed from the second reformate stream and combined with the first benzene-rich stream from the first reformate.

A key step of the overall process is the processing of the heavy fraction reformate to recover high purity paraxylene. The first xylene-rich stream is subjected to adsorption, isomerization and crystallization, preferably as follows: First, the xylene-rich stream is subjected to adsorption to preferentially remove paraxylene. The paraxylene-rich extract is subjected to crystallization to provide a high purity paraxylene product. The paraxylene-deficient raffinate is subjected to isomerization to convert xylenes to paraxylene. The raffinate and extract streams from the absorber are preferably subjected to fractional distillation prior to isomerization and crystallization, respectively, and one or more fractions from distillation are preferably recycled back to the adsorption stage.

In another broad aspect, the present invention is directed to an improved split feed process for reforming or aromatizing hydrocarbons, preferably a raw naphtha feed stream having a variable or fluctuating composition. In a more particular aspect, the invention includes the step of splitting a naphtha feed stream to provide a C7– light fraction and a C8+ heavy fraction. Preferably, the process includes the step of removing both the light ends and the heavy ends of the raw naphtha prior to splitting the naphtha into the C7– light fraction and C8+ heavy fraction. Preferably, the C8+ fraction includes most and preferably substantially all of the C8 and C9 paraffins, naphthenes and aromatics in the naphtha feedstock. Furthermore, it is desirable to remove all the C10's from the C8+ cut. Removal of the C10s can be part of the heavy ends removal step. However, because some of the C10 species have boiling points at atmospheric pressure that are similar or proximate to that of the C9 species, it may not be practical to remove all the C10 species from the C8+ cut by fractional distillation. Thus it is contemplated that, in accordance with this invention, the C8+ cut after distillation to removing C10's will contain about 15 wt % C10's. The resulting overhead C8–10 cut will have no more than about 15 wt % C10's. Thus, as used herein, the term "C8+ cut" or "C8+ fraction" broadly includes no more than about 15 wt % C10's, unless expressly stated otherwise.

In a preferred embodiment, a heavy fraction is reformed to provide a reformate with a surprisingly high octane number, preferably, an RON of 104+ or even 108+. A light fraction reformate is processed to provide a high purity benzene product, while the heavy fraction reformate is processed to provide a high purity paraxylene product. Although they may be combined or mixed, then separated into two different streams, the two reformate streams are preferably processed separately.

In another broad aspect, the invention is directed to a process for making high purity benzene and high purity paraxylene from a raw naphtha feedstock, including the steps of: (a) splitting a naphtha feed stream into a first feed stream comprising a light fraction and a second feed stream comprising a heavy fraction, said splitting being provided by distillation at a preselected cut point; (b) reforming the first feed stream in the presence of a first catalyst to provide a first reformate having a first preselected composition profile; (c) reforming the second feed stream in the presence of a second catalyst to provide a second reformate having a second preselected composition profile; and (d) adjusting the distillation cut point of step (a) in response to a limit point, wherein the limit point directly or indirectly reflects the composition of a stream downstream of the first or second catalyst.

In still another alternate embodiment, the process of this invention includes the steps of removing toluene and xylene from a light reformate stream produced from a light fraction, e.g., a C7− naphtha fraction, to provide a mixed aromatics stream, followed by separation of the toluene and xylene to provide a toluene-rich stream, followed by disproportionation and/or transalkylation of the toluene in the toluene-rich stream without extraction of the toluene-rich stream. Preferably, the light reformate stream is produced by non-acidic monofunctional catalytic aromatization of a C7− naphtha feed resulting from treatment of raw naphtha to remove light and heavy ends followed by C7−/C8+ splitting of the thus-treated naphtha.

In a further alternate embodiment of the invention, an integrated process for making high purity benzene and high purity paraxylene includes the following steps: (a) a pre-splitting treatment step, wherein a raw naphtha feed stream is treated to remove light ends and heavy ends from the raw naphtha feed stream, to provide a "middle-cut" naphtha feed stream; (b) a splitting step, wherein the middle-cut naphtha feed stream from step (a) is split into a C7− light fraction and a C8+ heavy fraction; (c) a monofunctional reforming step, wherein the light fraction is reformed in the presence of a first catalyst system to provide a first reformate stream that is rich in benzene and toluene; (d) a bifunctional reforming step, wherein the heavy fraction is reformed in the presence of a second catalyst system to provide a second reformate stream that is rich in mixed xylenes; (e) a light end adjustment step, wherein the removal of light ends is adjusted to remove more C6's from the raw naphtha feed stream, the light end adjustment being responsive to a benzene limit point; (f) a heavy end adjustment step, wherein the removal of heavy ends is adjusted to remove more C9's from the raw naphtha feed stream, the heavy end adjustment being responsive to a paraxylene limit point; and (g) a split feed adjustment step, wherein the cut point is adjusted in the splitting step, to provide either more or less C7's in the heavy fraction and either more or less C8's in the light fraction, the feed split adjustment step being responsive to the interdependent benzene limit point and paraxylene limit point.

A. Integrated Process

In one aspect, the invention is directed to an integrated process for making both high purity benzene and high purity paraxylene from a single naphtha feedstock. Broadly, the process includes the steps of providing first and second naphtha fractions; reforming the first and second naphtha fractions in the presence of first and second catalysts to provide first and second reformates, the first reformate being rich in benzene and toluene, the second reformate being rich in mixed xylenes. A first benzene-rich stream is removed from the first reformate.

One key step is forming the high purity benzene from the light fraction reformate. The first benzene-rich stream is separated into a light fraction and a heavy fraction, and the light fraction is recovered as a high purity benzene product. Simultaneously, a first xylene-rich stream is removed from the second reformate stream. A benzene-rich fraction is preferably removed from the second reformate stream and combined with the first benzene-rich stream from the first reformate.

Another key step is the recovery of high purity paraxylene from the heavy fraction reformate. The first xylene-rich stream is subjected to adsorption, isomerization and crystallization, preferably as follows: First, the xylene-rich stream is subjected to adsorption to preferentially remove paraxylenes. The paraxylene-rich extract is subjected to crystallization to provide a high purity paraxylene product. The paraxylene-deficient raffinate is subjected to isomerization to convert xylenes to paraxylene. The raffinate and extract streams from the absorber are preferably each subjected to fractional distillation prior to isomerization and crystallization, respectively, and the one or more fractions, e.g., an overhead fraction, from distillation is recycled back to the adsorption stage.

Among other factors, it has been discovered that the particular processing sequence described above simultaneously produces high purity paraxylene and high purity benzene from a fluctuating composition naphtha feedstock. Preferably, light and heavy ends are first removed from a raw petroleum naphtha feedstock, e.g., in sequential naphtha distillation units that remove C5−'s and C10+'s. The resulting C6–C9 naphtha feed is then fed to a feed splitter which has a C7−/C8+ cut point. Advantageously, as discussed in greater detail below, this cut point is adjusted in response to identified limit points in the benzene and paraxylene production trains. Moreover, we have discovered surprisingly good results using a sharp-cut separation between the light and heavy reformer feeds, such that C8+'s are minimized in the light fraction monofunctional reforming step, and C7−'s are minimized in the bifunctional reforming step. For example, we have discovered surprisingly high yields in both reformates, and in particular, a heavy fraction reformate with an RON of 104+ or even 108+.

Preferably, the process involves fractionating the two reformate streams separately. One reformate stream results from monofunctional reforming of the light C7− fraction, the other results from bifunctional reforming of the heavy C8+ fraction. The light fraction reformate is preferably sequentially fractionated to provide two separate toluene-rich streams, at least one of which can be disproportionated without intervening toluene extraction. The light fraction reformate is fractionated or otherwise separated to provide a benzene-rich stream and a toluene-rich stream. That toluene-rich stream is fractionated, preferably in a toluene/xylene splitter, to provide an additional toluene-rich stream and also a stream rich in mixed xylenes. The heavy fraction reformate stream is separately fractionated, for example, in a heavy reformate fractionator or splitter, to remove the mixed xylenes as a heavy reformate fraction. Preferably, this mixed xylene stream from the heavy reformate splitter is combined with the mixed xylene stream from the toluene/xylene splitter before the combined xylene-rich stream is treated to make a high purity paraxylene product.

Preferably, the process also includes the use of successive distillations of the light fraction reformate to remove toluene, then disproportionating and/or transalkylating the toluene. This is preferably done by reforming a C7− light fraction as described above to provide a reformate rich in benzene and toluene. This reformate is preferably fractionated as described above. One of the two toluene-rich streams discussed above is preferably directed to the disproportionation unit, without any intervening extraction.

B. Split Feed High Octane Reforming with Bifunctional Catalyst

An alternate embodiment of the invention is a process for making high purity benzene and high purity paraxylene, which includes the step of splitting a naphtha feed stream into a C7− light fraction and a C8+ heavy fraction, then reforming each fraction separately. The light fraction may be reformed (aromatized) in the presence of a non-acidic monofunctional catalyst, and the heavy fraction may be reformed (aromatized) in the presence of an acidic bifunctional catalyst.

In accordance with this process, the heavy fraction reformate has a surprisingly high concentration of aromatics, measured as octane number, specifically, an RON of 104 or above (104+) and preferably 106 or above (106+) or more preferably 108 or above (108+). Surprisingly, this high octane number is accomplished under conventional reforming conditions. That is, reforming is done at: pressures varying from 1 atmosphere to 500 psig, more preferably from 50 to 300 psig; a molar ratio of hydrogen to hydrocarbons from 1:1 to 10:1, more preferably from 2:1 to 6:1; temperatures from 400° C. to 600° C., preferably from 430° C. to 550° C.; and a liquid hourly space velocity of between 0.3 and 5.

As used herein, the "C7− fraction" comprises primarily C6's and C7's, but may contain up to about 10% C8+'s, and may also contain some C5−'s, although most of the C5−'s are preferably removed in the light ends removal step. As used herein, the "C8+ fraction" comprises primarily C8's and C9's, and may also contain some C10+'s, although most of the C10+'s are preferably removed in the heavy ends removal step. The C7−/C8+ split is preferably a "sharp cut" split. Typically, however, a perfect split is not possible, or at least not economical. Therefore, it is preferred that the C8+ heavy fraction contain no more than about 10% C7−'s and the C7− light fraction contain no more than about 10% C8+'s. Most importantly, the concentration of C7−'s in the heavy fraction should be restricted as much as is economically possible, so that the resulting heavy fraction reformate will have a high concentration of aromatics as reflected by octane number, e.g., an RON of 104+ or even 108+. As described elsewhere in this patent, the cut point selected for this C7−/C8+ split will depend mainly on the operating temperature selected in the naphtha feed splitter. Also, under certain conditions discussed below, the cut point will be adjusted, so that more C7−s are directed to the heavy reformer. It is understood that the RON of the heavy fraction reformate may tend to be lower during those times.

C. Feedstock Flexibility using Parallel Split Feed Reforming with Disproportionation and Transalkylation Yet another alternate embodiment of the invention includes a feature that provides for feedstock flexibility, i.e., an ability to handle wide swings in feedstock composition. In particular, the process is a split feed reforming process with a cut point adjustment step. This process preferably also includes removal of naphtha feed light ends (e.g., C5−'s) and heavy ends (e.g., C10+'s) and a naphtha feed C7/C8 splitting step, to continuously convert a naphtha feed stream having a fluctuating or variable composition to high purity benzene and high purity paraxylene. Broadly, according to this invention, the cut point is adjusted whenever a preselected limit point is reached. Among other factors, this embodiment is based on the discovery that a continuously adjustable or flexible cut point, which is adjusted or modified in response to one or more downstream limit points, simultaneously maximizes production of high purity benzene product and high purity paraxylene product without affecting product purity.

Preferably, the cut point adjustment step includes the step of monitoring one or more parts of the benzene and paraxylene processing trains, and identifying when a preselected limit point is reached. According to this particular embodiment, the C7−/C8+ cut point in the splitter is then adjusted in response to the identified limit point, to "shift" or "swing" the naphtha feed away from the source of the limit point. In accordance with the invention, when a preselected benzene limit point is reached and identified, the cut point in the feed splitter is adjusted in an amount sufficient to direct more C7's to the heavy fraction reformer. Conversely, when a paraxylene limit point is reached and identified, the cut point is adjusted in the opposite direction. That is, the distillation temperature in the feed splitter is raised in an amount sufficient to direct more C8's to the light fraction reformer.

In another specific embodiment of this invention, the cut point in the depentanizer, or the cut point in the heavy ends separator, or both, are adjusted in response to one of the limit points, preferably a downstream limit point. In a preferred embodiment, any adjustment in the cut point of the depentanizer or heavy ends separator is in addition to the adjustment in the C7−/C8+ cut point in the splitter.

An advantage of this continuously alternating cut point adjustment procedure is the ability to swing between production of benzene and paraxylene without sacrificing overall output. Because these adjustments are made at the front end of the process, where the naphtha is being fed to the system, the result is more controllable and consistent high purity benzene and high purity paraxylene products. Moreover, this feature provides one with an ability to continuously process naphtha with wide-ranging or fluctuating compositions.

Yet another advantage of the continuously alternating cut point adjustment process is that naphthas suitable for feedstock can have a surprisingly high variability in composition. For example, the paraffin content in the naphtha may range from about 45% to as much as 75% by weight. In addition, the naphtha feedstock may have a high variability in carbon number distribution. For example, it may have a C6–C7 hydrocarbon content ranging from about 45% to as much as 60% by weight and a C8–C9 hydrocarbon content ranging from about 30% to 60% by weight. Yet surprisingly, high purity benzene and high purity paraxylene are produced in spite of the undesirably high levels of paraffins and fluctuating carbon numbers in the raw naphtha feedstock.

D. Disproportionation of Unextracted Toluene

According to still another alternate embodiment of the present invention, a process for making high purity benzene and high purity paraxylene includes the step of subjecting an unextracted toluene-rich aromatics stream to a disproportionation step where the aromatics stream contains minor amounts of nonaromatics, e.g., anywhere from about 0.2% to about 5.0% total aromatics boiling in the BTX range, including paraffins, olefins and naphthenes.

In an alternate embodiment, a process for making and recovering high purity benzene and high purity paraxylene from a wide boiling point naphtha, comprises the steps of separately reforming a light naphtha fraction and a heavy naphtha fraction to form a light reformate rich in benzene and toluene and a heavy reformate rich in mixed xylenes; recovering paraxylene from the heavy reformate; removing a benzene-rich fraction from the light reformate and recovering benzene from the benzene-rich fraction; and removing a toluene-rich fraction from the light reformate, said toluene-rich fraction being treated to disproportionation or transalkylation without extraction to form benzene and xylenes in said toluene-rich fraction.

In another alternate embodiment, the process includes the steps of: (a) providing first and second naphtha fractions; (b) reforming said first and second naphtha fractions in the presence of first and second catalysts to provide first and second reformates, the first reformate being rich in benzene and toluene, the second reformate being rich in mixed xylenes; (c) recovering paraxylene from the second reformate; (d) fractionating the first reformate to provide a first benzene-rich stream and a first toluene-rich stream; (e)

fractionating the first toluene-rich stream to provide a second toluene-rich stream and a first xylene-rich stream; (f) subjecting the second toluene-rich stream to disproportionation and transalkylation without an intervening extraction step to convert at least a portion of the toluene in the second toluene-rich stream to benzene and mixed xylenes; and (g) recycling at least a portion of the unconverted toluene resulting from step (f) with the first reformate prior to the fractionation of step (d).

Among other factors, we have found that disproportionation of toluene in an aromatics stream is efficiently and effectively carried out without a separate extraction step, and also without undesirable levels of catalyst fouling, provided benzene and xylenes are first removed from the stream. Unexpectedly, it has been found that high purity benzene may be made from the disproportionation effluent produced from this unextracted toluene-rich stream. Surprisingly high purity benzene product may be made even when the unextracted toluene contains anywhere from about 0.2% to 5.0% total nonaromatics boiling in the BTX range, including paraffins, olefins and naphthenes.

In a more specific aspect, this process preferably includes reforming at least one hydrocarbon feed stream to provide a first product stream, where the first product stream has an aromatics component rich in benzene, toluene and xylene, and a nonaromatics component comprising paraffins (preferably no more than about 5% by weight paraffins that co-boil with toluene). That process also includes the further step of separating the first product stream into a toluene-rich stream and a xylene-rich stream (e.g., via a T/X splitter), then subjecting the unextracted toluene-rich stream (which still has a certain level of nonaromatics, e.g., as much as 5% by weight paraffins that co-boil with toluene) to disproportionation and/or transalkylation, resulting in a mixed aromatics stream (benzene, toluene and xylene). The mixed aromatics stream is then combined with the first product stream of step and is stabilized to remove light ends. Next, the stream of step (d) is separated into a benzene-rich stream and a benzene-lean stream.

BRIEF DESCRIPTION OF DRAWINGS

FIG. 8 is a block flow diagram of an alternate embodiment of the invention illustrating paraxylene recovery and finishing.

FIG. 9 is a block flow diagram of an alternate embodiment of the invention illustrating a method of processing unstabilized light aromatics.

DETAILED DESCRIPTION AND SPECIFIC EMBODIMENTS

Figure 1:
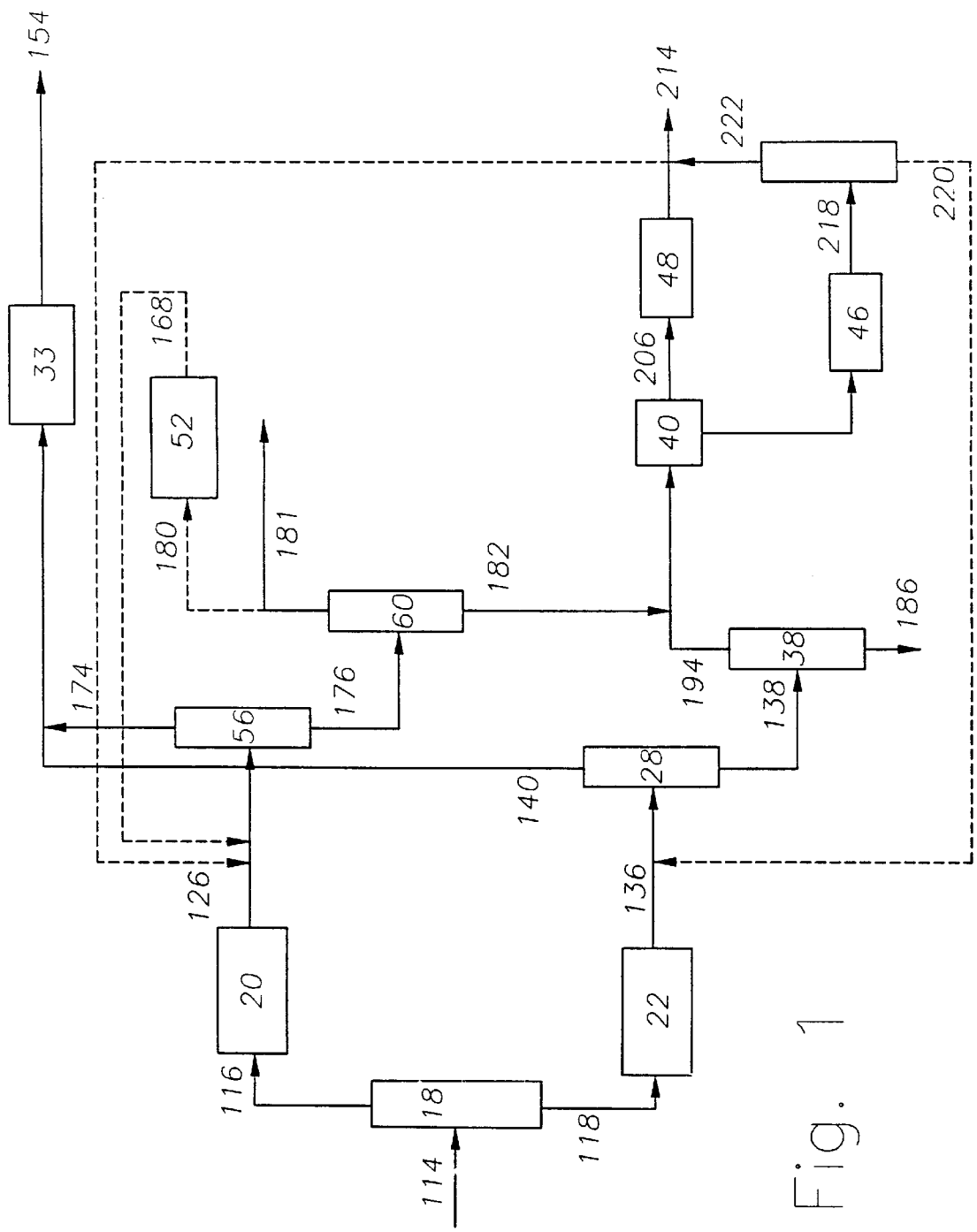
FIG. 1 is a block flow diagram of a specific embodiment of the invention illustrating a broad overall process flow.

The following discusses details and other aspects and features of the invention, including specific embodiments of the invention.

A. Integrated Process

As summarized above, this invention is broadly directed in one aspect to an improved process for simultaneously making high purity benzene and high purity paraxylene from a naphtha feedstock. The concentration of the benzene and paraxylene should be above about 99 wt %, preferably above about 99.5 wt %, and more preferably at least about 99.90%. In a most preferred embodiment, purity is extremely high, e.g., at least about 99.984 wt % benzene and at least about 99.90 wt % paraxylene. Broadly, the process includes the steps of providing first and second naphtha fractions; reforming the first and second naphtha fractions in the presence of first and second catalysts to provide first and second reformates, the first reformate being rich in benzene and toluene, the second reformate being rich in mixed xylenes; and removing a first benzene-rich stream from the first reformate, then separating the first benzene-rich stream into a light fraction and a heavy fraction, and recovering a high purity benzene product from the light fraction. Simultaneously, a first xylene-rich stream is removed from the second reformate stream. Also, preferably, a benzene-rich fraction is removed from the second reformate stream and combined with the first benzene-rich stream from the first reformate. The first xylene-rich stream is preferably subjected to isomerization to convert xylenes to paraxylene; to adsorption to separate out paraxylenes; and to crystallization to provide a high purity paraxylene product.

Preferably, according to an alternate embodiment of the invention, the integrated process involves making high purity benzene and high purity paraxylene, preferably at least 99.9% by weight, from a full boiling range naphtha. The process includes the following steps: (a) separating a hydrocarbon feed into a light reformer feed and a heavy reformer feed; (b) subjecting the light reformer feed from step (a) to catalytic aromatization to provide a first reformate stream comprising benzene and toluene; (c) separating the first reformate stream into a first benzene-rich stream and a first toluene-rich stream; (d) processing the first benzene-rich stream to produce a high purity benzene product; (e) separating the first toluene-rich stream into a second toluene-rich stream and a first xylene-rich stream; (f) subjecting the second toluene-rich stream to disproportionation; (g) subjecting the heavy reformer feed from step (a) to catalytic aromatization to provide a second reformate stream comprising aromatics (benzene, toluene, mixed xylenes, and C9 aromatics); (h) subjecting the second reformate stream to separation to provide a benzene-rich light fraction (the "third benzene-rich stream"), preferably comprising C7–'s, and a xylene-rich heavy fraction (the "second xylene-rich stream"), preferably comprising C8+'s; (i) separating the first and second xylene-rich streams into an enriched xylene-rich stream (the "third xylene-rich stream") and a first gasoline stream; (j) purifying the third xylene-rich stream by simulated moving bed adsorption separation into a first paraxylene-rich stream and a first paraxylene-deficient stream; (k) isomerizing the first paraxylene-deficient stream to produce an isomerate comprising mixed xylenes; and (l) crystallizing the first paraxylene-rich stream to produce a high purity paraxylene product.

Optionally, the hydrocarbon feed, in the form of full boiling range naphtha, is depentanized and hydrotreated to remove sulfur and nitrogen before being separated into a light reformer feed and heavy reformer feed. Preferably, the heavy naphtha (e.g., C10+'s) is also removed before the naphtha feed is hydrotreated. Preferably, the heavy reformer feed includes C9 paraffins and naphthenes in the naphtha feed, both of which have boiling points that overlap with the boiling points of C10 paraffins. Thus, the heavy naphtha that is removed should not include more C9's than necessary, so as to direct the C9's to the reforming step. The full boiling range naphtha should be hydrotreated before being depentanized or having the heavy naphtha removed, or both. Also preferably, the full boiling naphtha feed is hydrotreated before being separated into light and heavy reformer feeds.

Preferably, the reformer feeds should contain very little sulfur and nitrogen in order to prevent catalyst poisoning. Preferably, the raw feed is depentanized and heavy ends, e.g., C10+ materials, are removed before hydrotreating to remove sulfur and nitrogen. Preferably, the heavy reformer feed includes C9 paraffins and naphthenes and excludes most of the C10+ material. Since the boiling points of the C10 paraffins overlap those of the C9 components, one may decide to not include more C9 components in the heavy reformer feed than are necessary to make C9 aromatics feed for the toluene disproportionation. Alternatively, substantially all of the C9 components may be sent to the reformer, which, as discussed above, will probably inevitably include some C10 components having similar boiling points.

A preferred embodiment of the process involves the steps of depentenanizing some, and preferably most, of the naphtha feedstock to remove C5–'s, then removing the "heavy ends," but leaving the maximum amount of C9 aromatic precursors and preferably a stream composition having no more than about 15 wt % C10's. In this manner, the resulting "heart-cut" naphtha of this invention should still have those C9's that are useful for reforming to C9 aromatics, which can later be converted to xylenes in the toluene disproportionation reactor. That is, in accordance with this invention, the heartcut naphtha should include C9 paraffins and naphthenes, which are reformed to C9 aromatics, and which can later be converted to xylenes through subsequent processing, e.g., toluene disproportionation. The heartcut naphtha should be hydrotreated to reduce nitrogen and sulfur to the desired levels, then fed to the C7/C8 splitter to provide light and heavy feed streams for the respective reformers. If necessary or desirable, each reformer feed stream may then be treated to an additional desulfurization step to remove additional quantities of sulfur prior to reforming.

We have found that if a "sharp-cut" separation is made between the light and heavy reformer feeds such that C8+'s reformed by the monofunctional catalyst are minimized while at the same time C7–'s reformed by the bifunctional reforming step are also minimized, an improved product is made. We have discovered that the total yield of aromatics from the feed may be increased by matching the catalyst to the respective reformer feed composition, e.g., light or heavy reformer feed. Preferably, the sharp-cut separation of this invention involves no more than about 5% C7–'s in the heavy fraction. Ideally, the heavy fraction has no more than about 1% C7–'s and even more preferably, substantially no C7–'s, but those levels are not typically very practical or economical. However, by limiting the C7–'s in the heavy reformer feed, the bifunctional catalyst reformer may be operated at moderate conditions, but yield surprisingly higher yields of heavy aromatics. Any removal of the light ends as fuel gas represents a loss of hydrocarbons available to the process for making benzene or paraxylene. Therefore, by minimizing these losses while maximizing aromatic yields, the overall conversion to benzene and paraxylene is increased. More preferably, to further minimize cracking losses, the light reformer feed is aromatized in step (b) in the presence of hydrogen and a non-acidic catalyst comprising at least one Group VIII metal and a non-acidic zeolite support to produce the first reformate stream. It is noted, however, that in accordance with other aspects of the invention, there may be reasons, as discussed below in greater detail, from deviating from a C7–/C8+ sharp-cut, e.g., where for feed flexibility purposes the C7's are diverted due to a cut point adjustment.

In a specific embodiment of the invention, the process includes a stabilization step. In particular, before being separated into the benzene-rich stream and toluene-rich stream in step (c) above, the first reformate stream is stabilized by removing light non-aromatic hydrocarbons. Optionally and preferably, the first reformate stream is stabilized in the same stabilizer column with a disproportionated product stream from step (f) above, e.g., the two streams are combined. Preferably, the process produces a high purity benzene product that exceeds the ASTM Refined Benzene-545 standard. That is, benzene purity is greater than 99.90 wt %. Furthermore, the benzene product should have a toluene concentration of up to about 40 ppm by weight or less, which is substantially lower than the 500 ppm toluene level prescribed by Benzene-545. Finally, the non-aromatics concentration is as low as about 70 ppm or less by weight, which is substantially lower than the 1000 ppm nonaromatics level set forth in Benzene-545. In the benzene processing step (d) above, the first benzene-rich stream should be first selectively hydrogenated to hydrogenate diolefins and partially hydrogenate olefins, and can be mixed with the second and third benzene streams, which are discussed below, prior to selective hydrogenation and extractive distillation. The selective hydrogenation effluent is then extractively distilled to remove non-aromatics and further fractionated in a benzene distillation column to provide the high purity benzene product. Produced raffinate from the extractive process step may be recycled back to the naphtha feed, or more preferably, it is used as an octane blending component if a demand exists for gasoline blending streams. Preferably, the heavy fraction from the benzene recovery column is subjected to disproportionation in step (f), preferably after being mixed with the recycled toluene-rich stream (the "second toluene-rich stream" in step (e)), and C7− stream distilled overhead from the extract column and optionally a C9− stream distilled overhead from the heavy gasoline splitter, e.g., a distillation column.

Preferably, the separation of step (e) above is accomplished in a toluene/xylene ("T/X") splitter, e.g., a distillation column. The second toluene-rich stream is preferably disproportionated as discussed in the previous step (d), without extraction, and is combined with a heavy fraction from the benzene recovery column. The first xylene-rich stream in step (e) (comprising mixed xylenes) is preferably combined with a heavy fraction from the second reformate splitter. Preferably, the heavy reformer feed from step (a) is aromatized in step (g) above in the presence of hydrogen and an acidic catalyst. Optionally, but preferably, the disproportionation reactor effluent in step (f) is subjected to transalkylation to convert any C9 aromatics and toluene to xylenes.

In step (h), the second reformate stream is preferably separated to provide a benzene-rich light fraction (the "third benzene-rich stream"), preferably comprising C7−'s, and a heavy fraction (the "second xylene-rich stream"), preferably comprising C8+'s. Preferably, the separation of the second reformate stream is accomplished in a "reformate splitter," e.g., a distillation column to provide a sharp-cut that simultaneously minimizes the C8+'s in the benzene-rich light fraction and minimizes C7−'s in the second xylene-rich stream. Optionally, an imported reformate stream or mixed xylene stream, e.g., streams from another source or produced by another system, may be fed to the reformate splitter. Optionally, but preferably, a mixed reformate stream comprising an imported reformate or mixed xylenes and the second reformate stream is clay treated before being fed to a reformate splitter. Also, as discussed above in step (d), the third benzene-rich stream from the reformate splitter can be subjected to selective hydrogenation and extractive distillation. The extractive distillation product is subjected to further distillation to provide a light fraction of high purity benzene and a heavy fraction comprising C7−'s, which is then subjected to disproportionation and preferably transalkylation. Preferably, the C9− stream from the heavy gasoline splitter and, optionally, excess desorbent produced by step (j), is added to the disproportionation feed.

Step (i) preferably involves separating the first xylene-rich stream into an enriched xylene-rich stream (the "third xylene-rich stream") and a first gasoline stream. Preferably, the first xylene-rich stream is distilled to concentrate xylene content and is separated into an enriched stream (the "second xylene-rich stream") and a third benzene-rich stream. This distillation is accomplished in a "reformate splitter," e.g., a distillation column. Optionally, but preferably, the second xylene-rich stream is added to the feed to the xylene rerun column. The xylene rerun column further concentrates the xylene content of an overhead product (the "third xylene-rich stream") and a first heavy gasoline stream. Also, the first gasoline stream may be further distilled in a heavy gasoline splitter, e.g., distillation column, to remove a C9− stream that may be further processed to benzene and paraxylene by recycling to step (f) above.

Preferably, in step (j), the purified xylene-rich stream is from a simulated moving bed adsorber and is distilled to provide a desorbent (the "first internal recycle"), an overhead stream for recycle to disproportionation and a paraxylene-rich fraction (the "first paraxylene-rich fraction"). Optionally, but preferably, a paraxylene-lean fraction is separated in the raffinate column, into a desorbent (the "second internal recycle") and a paraxylene-deficient stream (the "first paraxylene-deficient stream"). Optionally, an overhead stream for recycle to disproportionation may be withdrawn from the raffinate column instead of from the extract column.

The isomerate of step (k) is preferably an equilibrium distribution of xylene isomers formed from the first paraxylene-deficient stream. Optionally, but preferably, the isomerate is distilled in a light aromatics separation column, e.g., distillation column, separating a gas stream for recovery, a second benzene-rich stream, and a fourth xylene-rich stream (the "fourth xylene-rich stream") for recycle to the xylene rerun column.

Preferably, the crystallization step of step (1) comprises two crystallization stages with internal mother liquor recycles. Optionally, step (1) may comprise one stage crystallization. Preferably, when two crystallization stages are used, the second-stage mother liquor is recycled to the xylene rerun column and the first-stage mother liquor is preferably sent to the second stage. Excess mother liquor is preferably recycled to the xylene rerun column. Preferably, the paraxylene crystals from the initial crystallization are subjected to a reslurry step, e.g., in a reslurry tank, then to a purification and washing step. Preferably, in the reslurry step, the paraxylene crystals are mixed with a recycle stream of filtrate or mother liquor from the purification and washing step. This recycle stream contains the impurities that are removed in the purification and washing step, and also contains some paraxylene.

Figure 13:
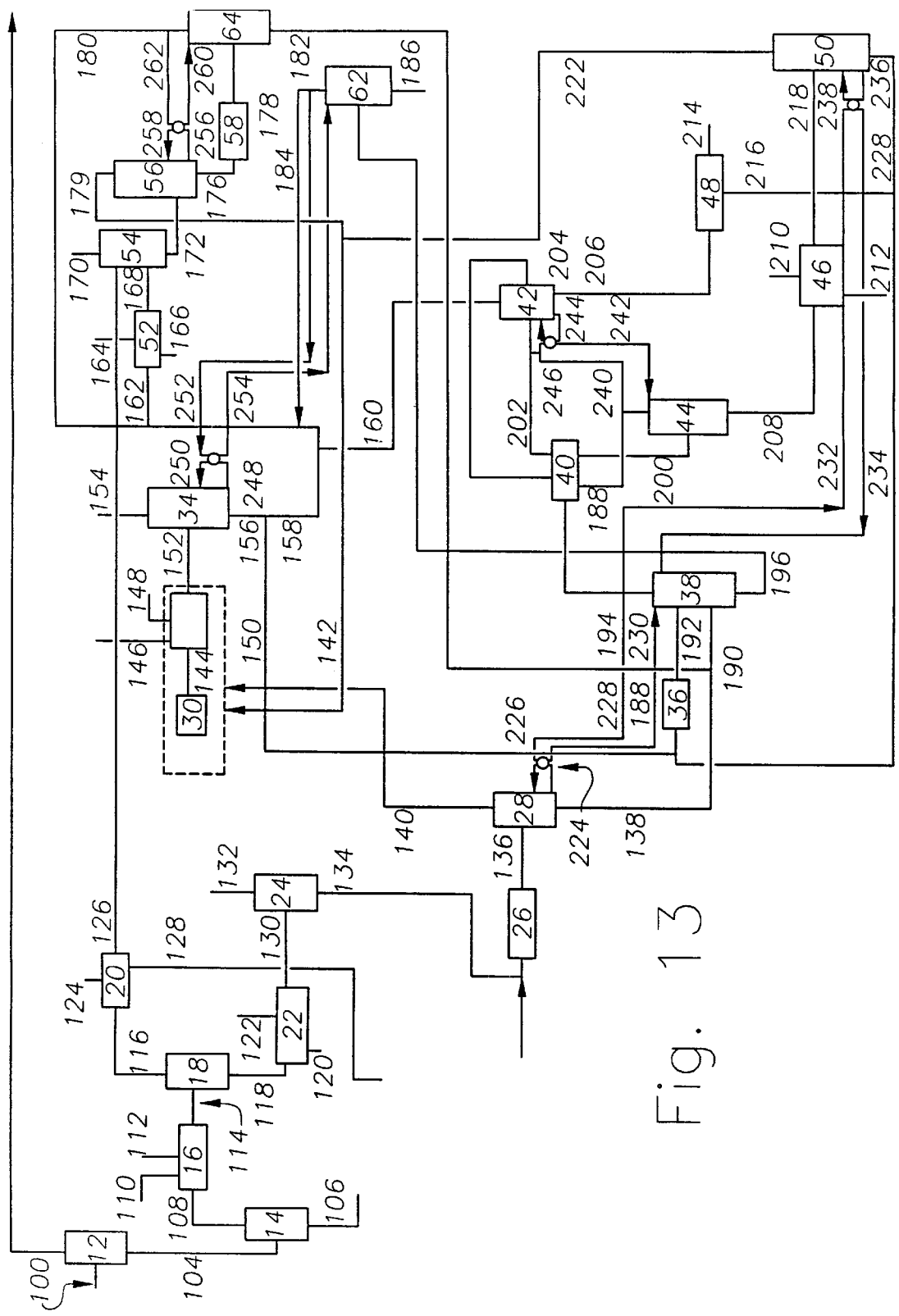
FIG. 13 is a block flow diagram of a specific embodiment of the invention illustrating an overall process flow, including a distillation heat integration arrangement.

In reference to FIG. 1, a process for making benzene and paraxylene from a hydrocarbon feed will be described. A more detailed illustration of an integrated process of this invention is shown in FIG. 13, and will be discussed below. Referring now to FIG. 1, the hydrocarbon feed 114 is preferably a full boiling naphtha that has been hydrotreated. More preferably, the hydrocarbon feed 114 has been depentanized to remove the C5− hydrocarbons and has also been distilled to remove any heavy naphtha, e.g., C10+'s. (See FIG. 10.) The hydrocarbon feed 114 is then distilled in a naphtha splitter 18 to provide a light reformer feed 116 to the monofunctional catalyst reformer 20 and a heavy reformer feed 118 to the bifunctional catalyst reformer 22. The light reformer feed 116 is then subjected to a catalytic aromatization in the reformer 20 to provide a first reformate stream 126 comprising benzene and toluene. The first reformate stream 126 is then separated in the benzene/toluene splitter 56 to provide a first benzene-rich stream 174 and a first toluene-rich stream 176. The first benzene-rich stream 174 is then processed or finished to provide a high purity benzene stream 154. The finishing steps 33 include clay treatment, selective hydrogenation, extraction, or distillation, alone or in combination. The first toluene-rich stream 176 is separated in the toluene/xylene splitter 60 into a second toluene-rich stream 181 and a first xylene-rich stream 182. Optionally, but preferably, the toluene-rich stream 181 is subjected to disproportionation in unit 52. The disproportionation effluent 168 is recycled to the distillation column 56.

The heavy reformer feed 118 is subjected to catalytic aromatization in reformer 22 to provide a second reformate stream 136. The second reformate stream 136 is separated in the reformate splitter 28 to provide the third benzene-rich stream 140 and the second xylene-rich stream 138. The third benzene-rich stream 140 is fed to the benzene finishing steps 33. The second xylene-rich stream 138 is separated in the xylene rerun column 38 to provide a third-xylene-rich stream 194 and a first gasoline stream 186. The third xylene-rich stream 194 is processed in a simulated moving bed adsorption unit 40 to provide a second paraxylene-rich stream 206 and a first paraxylene-deficient stream 208. The first paraxylene-deficient stream 208 is isomerized in the isomerization step 46 to provide an isomerate 218 comprising paraxylene and benzene. The isomerate 218 is separated in a light aromatics stabilizer column 50 to provide a fourth xylene-rich stream 220 for recycle to xylene rerun column 38 and a second benzene-rich stream 222 for recycle to the distillation column 56. The second paraxylene-rich stream 206 is crystallized in the crystallization unit 48 to produce a high purity paraxylene stream 214. Although a variety of crystallization methods may be used as part of crystallization unit 48, a preferred method involves crystallizing the paraxylene in the paraxylene-rich stream, removing a portion of the resultant mother liquor, contacting the paraxylene crystals with another stream containing paraxylene and some non-paraxylene impurities to form a "reslurry" to form a paraxylene suspension, then subjecting the paraxylene suspension to purification and washing, preferably involving washing of the suspension in a wash column or in a centrifuge. Advantageously, the stream containing impurities and paraxylene, which is combined with the paraxylene crystals from the crystallization stage to form a reslurry, is a recycle steam from the purification and washing stage. Certain aspects of preferred paraxylene purification and recovery steps are disclosed in application Ser. No. 08/875, 278.

Figure 2:
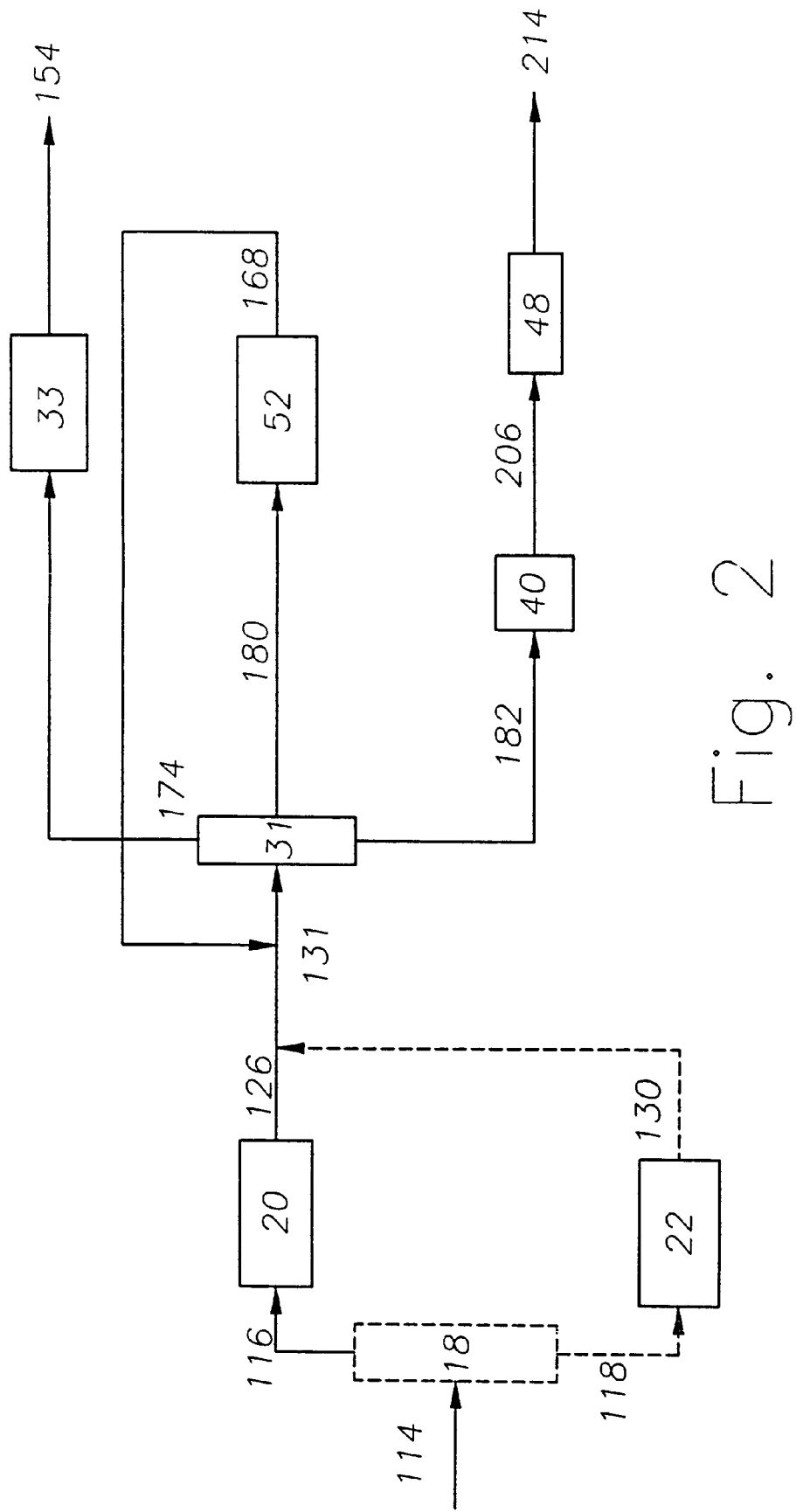
FIG. 2 is a block flow diagram of an alternate embodiment of the invention illustrating an overall process flow.

Referring to FIG. 2, a process for making high purity benzene and high purity paraxylene from a hydrocarbon feed will be described wherein reformates are combined. The hydrocarbon feed 114 is reformed using either a monofunctional catalyst or a bifunctional catalyst in a reformer 20 to provide one or more reformate streams 126, 130. The hydrocarbon feed 114 is separated in a naphtha splitter 18 to provide a light reformer feed 116 and a heavy reformer feed 118. The light reformer feed 116 is preferably reformed using a monofunctional catalyst in a reformer 20 to provide a light reformate stream 126. The heavy reformer feed 118 is reformed using a bifunctional catalyst in reformer 22 to provide a heavy reformate stream 130. The combined reformate streams 131 are fractionated in a distillation column 31 to provide a benzene-rich stream 174, a second toluene-rich stream 180, and a first xylene-rich stream 182. The second toluene-rich stream 180 is subjected to disproportionation to provide a mixed aromatics stream 168 which may be recycled to the distillation column 31. The benzene-rich stream 174 is processed or finished 33 to provide a high purity benzene stream 154. The finishing steps 33 may include extraction or distillation or both. The first xylene-rich stream 182 is subjected to adsorption 40 to provide a second paraxylene-rich stream 206 which is further purified by crystallization unit 48 to provide a high purity paraxylene 214.

B. Split Feed High Octane Reforming with Bifunctional Catalyst

An alternate embodiment of the invention is a process which includes the step of splitting a naphtha feed stream into a C7– light fraction (comprising C7–'s) and a C8+ heavy fraction (comprising C8+'s), then reforming each fraction separately. The light fraction may be reformed (aromatized) in the presence of a non-acidic monofunctional catalyst, and the heavy fraction is preferably reformed (aromatized) in the presence of an acidic bifunctional catalyst In accordance with this embodiment of the process, the heavy fraction reformate has a surprisingly high concentration of aromatics, measured as octane number, specifically, an RON of 104 or above (104+) and preferably 108 or above (108+). Surprisingly, this high octane number is accomplished under conventional reforming conditions, that is, at pressures varying from 1 atmosphere to 500 psig, more preferably from 50 to 300 psig; molar ratio of hydrogen to hydrocarbons from 1:1 to 10:1, more preferably from 2:1 to 6:1; temperatures from 400 C. to 600 C., preferably from 430 C. to 550 C.; and liquid hourly space velocity of between 0.3 and 5.

In accordance with the invention, the conversion to aromatics of C8, C9 and C10 paraffins in the heavy fraction bifunctional reformer should be maintained at high levels, preferably at least about 90% or 95% and more preferably close to 100% conversion, that is, at least about 98% conversion. In accordance with this invention, when the C6 and C7 hydrocarbons are removed from the naphtha feed to the bifunctional reformer, the result is a surprisingly high selectivity to aromatics for the C8, C9 and C10 hydrocarbons that are present in the bifunctional reformer feed. In addition, these high aromatics selectivities are achieved at lower reformer catalyst average temperatures, than if the C6 and C7 hydrocarbons had been present in the feed, e.g., less than about 1000° F., and preferably less than 900° F. Furthermore, by aromatizing the C6 and C7 paraffins over a non-acidic catalyst such as Pt/K-Ba L Zeolite, the C6 and C7 paraffin conversion and selectivities are surprisingly higher than they are in acidic bifunctional reformers, resulting in higher yields of C6 and C7 aromatics, i.e., benzene and toluene. Moreover, such benzene and toluene are formed separately, as part of the benzene recovery train, as opposed to the xylenes, formed in the paraxylene recovery train.

It has also been discovered that a non-acidic catalyst has an adverse effect on production of paraxylenes. Thus, the light reformer feed should contain a minimum of C8+ hydrocarbons to be subjected to a non-acidic catalyst reforming. The light reformer feed is subjected to catalytic aromatization at elevated temperatures in the monofunctional catalyst reformer in the presence of hydrogen and using a non-acidic catalyst comprising at least one Group VIII metal and a non-acidic zeolite support, preferably platinum on a non-acidic zeolite L support, to produce the first reformate stream. The heavy reformer feed may be subjected to catalytic aromatization at elevated temperatures in a second reformer in the presence of hydrogen and using an acidic catalyst comprising at least one Group VIII metal and a metallic oxide support, preferably a non-presulfided acidic catalyst comprising platinum and tin on an alumina support, to produce a second reformate stream. It has also been discovered that when the heavy and light reformer feeds are aromatized as described above, the total amount of C8 aromatics produced in the first and second reformers as ethylbenzene is less than 20% by weight. Additionally, it has been discovered that more than 20% by weight of the total amount of xylenes produced are paraxylenes.

One of the catalysts that may be used as the non-acidic or monofunctional reformer catalyst has a non-acidic zeolite support charged with one or more dehydrogenating constituents. Among the zeolites useful in the practice of the present invention are zeolite L, zeolite X, and zeolite Y. These zeolites have apparent pore sizes on the order of 7 to 9 Angstroms. Zeolite L is a synthetic crystalline zeolitic molecular sieve which may be written as:

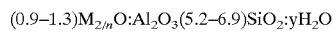

wherein M designates a cation, n represents the valence of M, and y may be any value from 0 to about 9. Zeolite L, its X-ray diffraction pattern, its properties and method for its preparation are described in detail in U.S. Pat. No. 3,216,789, which is hereby incorporated by reference to the extent it is not inconsistent with the present invention. The specific formula of the synthetic crystalline zeolitic molecular sieve may vary without changing the crystalline structure. For example, the mole ratio of silicon to aluminum (Si/Al) may vary from 1.0 to 3.5.

Zeolite X is a synthetic crystalline zeolitic molecular sieve which may be represented by the formula:

$$(0.7-1.1)M_{2/n}O:Al_2O_3(2.0-3.0)SiO_2:yH_2O$$

wherein M represents a metal, particularly alkali and alkaline earth metals, n is the valence of M and y may have any value up to about 8 depending on the identity of M and the degree of hydration of the crystalline zeolite. Zeolite X, its X-ray diffraction pattern, its properties and method for its preparation are described in detail in U.S. Pat. No. 2,882,244, which is hereby incorporated by reference to the extent it is not inconsistent with the present invention to show a zeolite useful in the present invention.

Zeolite Y is a synthetic crystalline zeolitic molecular sieve which may be written as:

$$(0.7-1.1)Na_2O:Al_2O_3:xSiO_2:yH_2O$$

wherein x is a value greater than 3 up to about 6 and y may be a value up to about 9. Zeolite Y has a characteristic X-ray powder diffraction pattern which may be employed with the above formula for identification. Zeolite Y is described in more detail in U.S. Pat. No. 3,130,007, which is hereby incorporated by reference to the extent it is not inconsistent with the present invention to show a zeolite useful in the present invention.

The zeolitic catalysts according to the invention are charged with one or more Group VIII metals, e.g., nickel, ruthenium, rhodium, palladium, iridium or platinum. The preferred Group VIII metals are iridium and platinum, which are more selective with regard to dehydrocyclization and are also more stable under the dehydrocyclization reaction conditions than other Group VIII metals.

The preferred percentage of platinum in the monofunctional or dehydrocyclization catalyst is between 0.1% and 5%, the lower limit corresponding to minimum catalyst activity and the upper limit to maximum activity. This allows for the high price of platinum, which does not justify using a higher quantity of the metal since the result is only a slight improvement in catalyst activity.

Group VIII metals are introduced into the large-pore zeolite by synthesis, impregnation or exchange in an aqueous solution of appropriate salt. When it is desired to introduce two Group VIII metals into the zeolite, the operation may be carried out simultaneously or sequentially. By way of example, platinum can be introduced by impregnating the zeolite with an aqueous solution of tetrammineplatinum (II) nitrate, tetrammineplatinum (II) hydroxide, dinitrodiamino-platinum or tetrammineplatinum (II) chloride. In an ion exchange process, platinum can be introduced by using cationic platinum complexes such as tetrammineplatinum (II) nitrate.

An optional element of the present invention is the presence of an alkaline earth metal in the monofunctional catalyst. That alkaline earth metal can be either barium, strontium or calcium. Preferably the alkaline earth metal is barium. The alkaline earth metal can be incorporated into the zeolite by synthesis, impregnation or ion exchange. Barium is preferred to the other alkaline earths because the resulting catalyst has high activity, high selectivity and high stability.

An inorganic oxide may be used as a carrier to bind the large-pore zeolite containing he Group VIII metal. The carrier can be a natural or a synthetically produced inorganic oxide or combination of inorganic oxides. Typical inorganic oxide supports which can be used include clays, alumina, and silica, in which acidic sites are preferably exchanged by cations that do not impart strong acidity.

The non-acidic catalyst can be employed in any of the conventional types of equipment known to the art. It may be employed in the form of pills, pellets, granules, broken fragments, or various special shapes, disposed as a fixed bed within a reaction zone, and the charging stock may be passed therethrough in the liquid, vapor, or mixed phase, and in either upward or downward flow. Alternatively, it may be prepared in a suitable form for use in moving beds, or in fluidized-solid processes, in which the charging stock is passed upward through a turbulent bed of finely divided catalyst.

An acidic catalyst is used in conjunction with the non-acidic catalyst. The acidic catalyst can comprise a metallic oxide support having disposed therein a Group VIII metal. Suitable metallic oxide supports include alumina and silica. Preferably, the acidic catalyst comprises a metallic oxide support having disposed therein in intimate admixture a Group VIII metal (preferably platinum) and a Group VIII metal promoter, such as rhenium, tin, germanium, cobalt, nickel, iridium, rhodium, ruthenium and combinations thereof. More preferably, the acidic catalyst comprises an alumina support, platinum, and rhenium. A preferred acidic catalyst comprises platinum and tin on an alumina support. A preferred acidic catalyst comprises platinum, tin and chlorine on an alumina support. The typical chlorine content of such a catalyst is about 1 wt %. Preferably, the acidic catalyst has not been presulfided before use. On the other hand, if one can insure no sulfur contamination of the non-acidic catalyst from the reformate produced by the acidic catalyst, then one might be able to use a presulfided catalyst, such as Pt/Re on alumina.

The reforming in both reformers is carried out in the presence of hydrogen at a pressure adjusted to favor the dehydrocyclization reaction thermodynamically and to limit undesirable hydrocracking reactions. The pressures used preferably vary from 1 atmosphere to 500 psig, more preferably from 50 to 300 psig, the molar ratio of hydrogen to hydrocarbons preferably being from 1:1 to 10:1, more preferably from 2:1 to 6:1.

In the temperature range of from 400° C. to 600° C., the dehydrocyclization reaction occurs with acceptable speed and selectivity. If the operating temperature is below 400° C., the reaction speed is insufficient and consequently the yield is too low for industrial purposes. When the operating temperature of dehydrocyclization is above 600° C., interfering secondary reactions such as hydrocracking and coking occur, and substantially reduce the yield. It is not advisable, therefore, to exceed the temperature of 600° C. The preferred temperature range (430° C. to 550° C.) of dehydrocyclization is that in which the process is optimum with regard to activity, selectivity and the stability of the catalyst. The liquid hourly space velocity of the hydrocarbons in the dehydrocyclization reaction is preferably between 0.3 and 5.

C. Feedstock Flexibility using Parallel Split Feed Reforming with Disproportionation and Transalkylation An alternate embodiment of the invention includes one or more features that provide for feedstock flexibility. In particular, the process is a split feed reforming process with a cut point adjustment step. Broadly, according to this embodiment, the cut point is adjusted whenever a preselected limit point is identified. In a further embodiment, the light and heavy ends of the raw naphtha are removed prior to reforming. Preferably, the cut point adjustment step includes the step of monitoring one or more parts of the benzene and paraxylene processing trains, and identifying when a preselected limit point is reached.

As summarized above, in a broad aspect, the invention is directed to a process for making high purity benzene and high purity paraxylene from a raw naphtha feedstock, including the steps of: (a) splitting a naphtha feed stream into a first feed stream comprising a light fraction and a second feed stream comprising a heavy fraction, said splitting being provided by distillation at a preselected cut point; (b) reforming the first feed stream in the presence of a first catalyst to provide a first reformate having a first preselected composition profile; (c) reforming the second feed stream in the presence of a second catalyst to provide a second reformate having a second preselected composition profile; and (d) adjusting the distillation cut point of step (a) in response to a limit point, wherein the limit point directly or indirectly reflects the composition of a stream downstream of the first or second catalyst.

In a specific embodiment, the limit point reflects a substantial change in the preselected composition profile of the first reformate. In another specific embodiment, the first feed stream is a C7− stream and the cut point is adjusted to provide for more C7−'s in the second feed stream; and the second feed stream is a C8+ stream and the cut point is adjusted to provide for more C8+−'s in the first feed stream.

The term "limit point" broadly refers to a predetermined condition within the process that is measurable and that is known to correspond to another condition within the process that is a "bottleneck" or "pinch point," or to a predetermined condition that is a bottleneck or pinch point itself. Preferably, as used herein, the limit point can be a benzene limit point or a paraxylene limit point. In a specific embodiment, the benzene limit point is the concentration of benzene and toluene in the light fraction reformate; and the paraxylene limit point is the concentration of mixed xylenes in the heavy fraction reformate. Those concentrations can be measured by conventional means, e.g., by gas chromatograph. Another limit point is the purity of the final benzene and paraxylene products. That is, when the benzene product purity falls below the specified level, a benzene limit point is deemed to be reached. The limit point can also be considered some combination of time and stream composition. For example, the limit point may be reached whenever the monofunctional reformate has unacceptably low levels of benzene over a predetermined number of hours, possibly indicating that the monofunctional catalyst has reached its limit for converting naphtha to benzene. Alternatively, the limit point may broadly refer to any other set point that reflects, directly or indirectly, the product yield or product purity. The step of identifying a limit point may also involve directly measuring the composition of the naphtha feedstream that is being fed to the naphtha splitter, then using those measured values to calculate or estimate certain downstream compositions that are known to create a limit point, e.g., a bottleneck. As another alternative, the benzene and paraxylene limit points can be when the light and heavy reformate productions are at their maximums. As yet another alternative, the limit point can be the point at which one of the reformers reaches its maximum reforming capacity or some predetermined point or condition that can be measured and that is related to capacity. A limit point can be reached, for example, when the reformer equipment is incapable of converting any more feed to reformate. This can be identified empirically, e.g., by an operator during actual operations. For example, in a specific embodiment, a limit point is reached when either the light or heavy reformate production is determined to be at a maximum and/or when the reformer equipment is determined to be incapable of converting any more feed to reformate. In that case, the limit point can be considered to be based on reformate composition, typically over some period of time, i.e., more than a sudden instantaneous spike in composition.

An alternative embodiment illustrating feed flexibility uses a feed-forward control scheme, wherein adjustments in the in-coming naphtha flow rate and the cut point(s) in the feed fractionation section are made in response to changes in the naphtha composition. Typically, these adjustments will be guided or made directly by computer. The analysis of the naphtha may be done, for example, by gas chromatography, mass spectroscopy, or near infrared spectroscopy or combinations thereof. Instead of a chemical analysis, a standard distillation of the incoming naphtha such as the ASTM D86 test may also be used to set the naphtha flow rate and the cut points in the feed fractionation section. The cut points adjusted are preferably those of the C5/C6 splitter (e.g., removal of light ends or depentanizer), the C7/C8 splitter and the C9/C10 splitter (e.g., removal or heavy ends). The object of this control system is to maintain within certain pre-defined limits the flow rates of benzene and toluene precursors to the light naphtha reformer and C8 and C9 aromatics precursors to the heavy naphtha reformer.

In this embodiment, the reforming products are also analyzed. The reactor inlet temperatures in both the light feed and heavy feed reformers are adjusted to compensate for catalyst aging and changes in the reactivity of the feed due to changes in the paraffin/naphthene ratio. As this control scheme maintains a nearly constant production of aromatics of each carbon number, there will preferably be fewer adjustments that need to be made in the downstream aromatics processing units. Intermediate tankage between the various process steps can be used to further smooth out any variability in the process. The optimum amount of intermediate tankage can be established by cost/benefit analysis.

According to one particular embodiment, the C7−/C8+ cut point in the splitter is then adjusted in response to the identified limit point, to "shift" or "swing" the naphtha feed away from the source of the limit point. The term "cut point" is itself well-known in the art, and is explained in several patents that have been incorporated by reference. The term "cut point" as used herein refers to a boiling point of the heaviest component released as part of the overhead from a splitter or fractionator. In a specific embodiment of this invention, a "normal" or "baseline" cut point is about 235° F., which refers to the "split" in the naphtha splitter or tower before any adjustment of cut point is made in response to predetermined applicable limit points. This means, in other words, the splitter is generally operated at a temperature such that all or substantially all of the components in the naphtha feed having a normal boiling point of about 235° F. and below are removed as overhead, i.e., as the light fraction. Substantially all of the components having a normal boiling point above about 235° F. are removed as bottoms, i.e., as the heavy fraction. The baseline cut point can be varied, depending on various factors, particularly the yield of the light naphtha and heavy naphtha. For example, a baseline cut point can be selected within the range from about 180° F. to about 300° F., and, more narrowly, within the range of about 230° F. to about 240° F. Generally, it is contemplated that a cut point of 235° F. corresponds to the C7−/C8+ split discussed above.

In accordance with this embodiment of this invention, the limit point should alternate. For example, at certain times or under certain processing conditions, the limit point will be a benzene limit point, while at other times or under processing conditions, the limit point is a paraxylene limit point. In each case, the terms "benzene limit point" and "paraxylene limit point" refer respectively to some limit point in the respective processing trains i.e., the train for producing high purity benzene and the train for producing high purity paraxylene, which are described in greater detail elsewhere.

The benzene limit point may reflect the capacity of the light fraction monofunctional reformer. For example, a benzene limit point may occur when coking levels in the reformer are undesirably high, or possibly when the catalyst is fully loaded with paraffins, or any other condition where the reformer can no longer convert the hydrocarbons in the light fraction feed to benzene or toluene. Alternatively, it may occur when the conversion levels are relatively stable or undesirably low. Alternatively, a benzene limit point may reflect some condition downstream of the light fraction reformer that represents a "bottleneck" or "pinch point." For example, the percentage of non-aromatics in the benzene product may be increasing over time, which may reflect that capacity of aromatics is exceeded.

Similarly, the paraxylene limit point may reflect a limitation on the capacity of the heavy fraction bifunctional reformer. As with the benzene limit point, the paraxylene limit point may be the point when the catalyst can no longer convert the hydrocarbons in the heavy fraction feed to mixed xylenes, or when the conversion levels are relatively stable or undesirably low. As with the benzene limit point, however, the paraxylene limit point may also be selected to reflect some condition downstream of the reformer, e.g., any other set point in the paraxylene processing or finishing train.

In accordance with another aspect of the invention, when a preselected "benzene limit point" is reached and identified, the cut point in the feed splitter can be adjusted, for example, in an amount sufficient to direct more C7's or other components that are part of the light fraction, to the heavy fraction reformer. Typically, this means the temperature profile in the distillation tower is lowered, causing fewer C7's to be vaporized and fewer C7's to leave the distillation unit as overhead, i.e., as part of the light fraction. Consequently, more C7's will remain as liquid and leave the distillation unit as bottoms, i.e, as part of the heavy fraction. The result of this adjustment is to remove the limit, e.g., to relieve the reforming burden on the light fraction reforming unit. This adjustment of the cut point may be performed in conjunction with other steps such as increasing the temperature of the light fraction reformer to increase the yield of benzene.

Conversely, when a "paraxylene limit point" is reached and identified, the cut point is adjusted in the opposite direction. That is, the distillation temperature profile in the feed splitter is raised in an amount sufficient to direct more C8's to the light fraction reformer. More C8's are vaporized and fewer C8's remain as liquid. Preferably, in a specific embodiment of the invention, adjustments are also made to the temperatures at which the light ends and the heavy ends are removed. These adjustments are also made in response to the benzene and/or paraxylene limit points discussed above.

In accordance with a specific embodiment of the invention, the baseline cut point is adjusted in response to certain limit points, which are discussed in greater detail below. When a benzene limit point is reached, the cut point is adjusted to a "low cut point," defined herein as a boiling point lower than the baseline or normal cut point. When a paraxylene limit point is reached, the cut point is adjusted to a "high cut point," defined herein as a boiling point higher than the baseline or normal cut point. This has the result of shifting one or more components from one reformer feed to the other reformer feed. As an example, when a benzene limit point is reached, the cut point is adjusted from the baseline cut point, e.g., about 235° F., to a lower cut point, e.g., about 180° F. This results in more C7's being shifted to the bottoms, leaving to become part of the heavy fraction reformer feed. On the other hand, when a paraxylene limit point is reached, the cut point is adjusted from the baseline cut point, e.g., about 235° F., to a higher cut point, e.g., about 300° F. This results in more C8's being shifted to the overhead, leaving to become part of the light fraction reformer feed. As discussed elsewhere in this application, this shift in reformer feed compositions is expected to affect the reformate; however, both reformers are capable of reforming both C7's and C8's. One of the advantages of this dynamic cut point adjustment system is that there is less of a need or reason to change the overall rate or amount of naptha being fed to the splitter.

In a preferred embodiment, a conventional feedback loop is used to implement the cut point adjustment feature of this invention. The actual feedback system used is not particularly critical, and any number of conventional feedback loop systems may be used. Broadly, the feedback loop system includes a sensor for measuring a benzene limit point and a sensor for measuring a paraxylene limit point, e.g., a device for measuring the reformate stream compositions, such as a gas chromatograph The system sends a signal to a temperature controller associated with the naphtha splitter when one of the limit points is reached; the temperature of the naphtha splitter is adjusted accordingly. That is, for a particular predetermined benzene limit point, the operating temperature of the naphtha splitter is adjusted in a predetermined manner to a predetermined adjusted operating temperature. Similarly, for a particular predetermined paraxylene limit point, the operating temperature is adjusted in a predetermined manner to a different predetermined operating temperature. In a specific embodiment, the adjusted temperature in the splitter, i.e., the temperature to which the cut point is adjusted in response to the limit point, depends on the "baseline" temperature of the splitter. It also depends on the naphtha feed composition and on the desired compositions of the light and heavy fractions, which, of course, vary depending on a particular feedstock being used. The baseline temperature is the temperature at which the naphtha splitter is operated without the presence of benzene or paraxylene limit points. The baseline temperature is dependent on the design of the particular splitter used to provide light fraction and heavy fraction reformer feedstreams, as well as on the composition of the naphtha feed and the desired compositions of the light fraction and the heavy fraction, which are directed, respectively, to the monofunctional light fraction reformer and to the bifunctional heavy fraction reformer.

Preferably, the C7−/C8+ cut point in the splitter is adjusted in response to the identified limit point. The cut point can be adjusted in a number of ways, including, for example, by a control system in which the operating temperature of the naphtha splitter is automatically adjusted based on input relating to the preselected limit points. In an alternative embodiment, the temperature of the splitter is manually adjusted to adjust the cut point, in response to a predetermined benzene limit point or a predetermined paraxylene limit point. By "predetermined," it is meant that a determination is made beforehand what the benzene limit point is and what the paraxylene limit point is. In accordance with a specific embodiment of the invention, a correlation is made between those predetermined limit point values (e.g., reformate stream compositions) and the cut point or operating temperature of the naphtha splitter.

An advantage of this continuously alternating cut point adjustment procedure is the ability to alter the relative amounts of benzene and paraxylene being produced without sacrificing overall output or product purity. Because these adjustments are made at the front end of the process, where the naphtha is being fed to the system, the result is more controllable and consistent high purity benzene and high purity paraxylene products. Moreover, one has an ability to continuously process naphtha with wide-ranging fluctuating compositions, and keep both reformers running at or near their maximum feed rates.

An important advantage of the continuously alternating cut point adjustment process is that naphthas suitable for feedstock can have a surprisingly high variability in composition, particularly in paraffin content. For example, the paraffin content in the naphtha may range from about 45% to as high as 75% by weight. In addition, the naphtha feedstock may have variable carbon number distribution. For example, it may have a C6–C7 hydrocarbon content ranging from about 45% to as much as 60% by weight and a C8–C9 hydrocarbon content ranging from about 30% to 60% by weight. Yet, surprisingly, high purity benzene and high purity paraxylene are produced in spite of the undesirably high levels of paraffins and fluctuating carbon numbers in the raw naphtha feedstock.

This cut point adjustment is preferably used in conjunction with a dual catalyst split feed process. It has been discovered that directing the naphtha feed to two separate reformers results in a "dampening" of changing loads resulting from changing feedstock compositions. By operating the reformers in parallel, a light reformer feed and a heavy reformer feed may be further channeled or funneled by diverting selected components to either the monofunctional catalyst reformer or the bifunctional catalyst reformer based on the naphtha feed characteristics. For example, if the naphtha feedstock contains a particularly high amount of C6 and C7 hydrocarbons, some of the C7 hydrocarbons can be diverted to the bifunctional catalyst reformer. Conversely, if the naphtha feedstock contains a low amount of C6 and C7 hydrocarbons, some of the C8 hydrocarbons could be diverted to the monofunctional catalyst reformer.

Further, it has been found that a relatively new monofunctional catalyst comprising platinum on halogenated L-zeolite exhibits greatly improved stability when processing feeds containing C8 and heavier components. The improved stability is obtained without sacrificing aromatics yield. As a result, either of the two reformers used in this embodiment of the invention may be used to react C8 components. Since in this embodiment of the invention the two reformers have an overlapping capability, the naphtha splitter may be used to funnel C8 paraffins to whichever reformer is least loaded.

This alternate embodiment of the invention is further based on our finding that if key pieces of equipment have overlapping capabilities, they can provide the extra needed capacity necessary for a varying feedstock without experiencing turn-down problems, e.g., control problems. For example, within an overall process to maximize benzene and paraxylene production, by combining the parallel split feed reforming with a disproportionation step including transalkylation, a pure toluene feed to a mix of toluene and C9 aromatics, including up to about 50% by weight of C9 aromatics may be fed to the disproportionation step. This overlapping capability to handle C7 and C9 aromatics by the disproportionation reactions within the disproportionation step also facilitates the capability of the method to handle a highly variable feedstock composition with a minimum of overcapacity in the design and fewer turn-down problems. For example, by combining the funneling of the feedstock with the overlapping of capabilities of the light feed and heavy feed reformers; the naphthas suitable for feedstock may possess a wide range of parameters. For example, the naphtha may have 45–75 wt % paraffins; 0–30 wt % C5 hydrocarbons; 15–23 wt % C6 hydrocarbons; 45–60 wt % C6 & C7 hydrocarbons; 20–35 wt % C8 hydrocarbons; 10–25 wt % C9 hydrocarbons; 0–20 wt % C10+ hydrocarbons and 0–5% hydrocarbons with boiling points of 360° F.+.

Preferably, the distillation of the full boiling range naphtha feed in step (a) provides for the removal of light hydrocarbons up to and including C6 hydrocarbons. The distillation may optionally remove only C5– hydrocarbons. Such flexibility provides for C6 components to be processed in the aromatics complex or elsewhere or stored whenever benzene handling capability of the aromatics complex is limited. Preferably, heavy components are removed in the same distillation step. This distillation step provides control over both the light and heavy components of the naphtha feed, thereby diminishing the variability in the feed composition. The control flexibility over the heavy components of the naphtha feed gives the processors the ability to maximize the recovery of C9 aromatics in the complex to increase the paraxylene yield. Optionally, C9+ hydrocarbons are removed from the naphtha in order to concentrate the xylenes in the feed whenever the bifunctional catalyst reformer or the disproportionation capacity of the aromatics complex becomes limiting, e.g., a limit point is reached. In addition, control over the light components allows the process of this invention to maximize benzene production by distilling overhead only the C5– hydrocarbons. However, whenever there is a limit in the benzene production capability of the aromatics complex or a high concentration of C6– hydrocarbons in the feed, the process of this invention may involve removing some or all of the C6 hydrocarbons and some of all of the lighter hydrocarbons overhead in the distillation step. Thus, the process of the invention maximizes paraxylene and benzene production simultaneously. Lastly, the naphtha containing C10+ components that could potentially harm downstream processing units in the aromatics complex are removed upstream of the complex for improved capacity utilization. These naphtha feed distillation steps allow for better management of the naphtha feed to maintain the complex at full paraxylene and benzene production, irrespective of the feed composition.

Among other factors, it has been discovered that if the naphtha feed is conditioned by removing the extreme light and heavy components before the reforming step, then conversion to the preferred aromatics is improved despite the use of widely varying feedstocks. This dampening effect also increases the flexibility to process a wide range of naphtha feeds with minimum over-capacity in the design. Preferably, this step removes C1–C5 hydrocarbons. Optionally, isohexane and other C6 hydrocarbons are also removed from the feed depending on the feedstock composition or downstream processing considerations, e.g., the presence of limit points. In addition, some or all of the C9+ hydrocarbons may also be removed. Preferably, this step removes C10+ hydrocarbons. Optionally, C9 hydrocarbons are also removed from the feed depending on the feedstock composition or downstream processing considerations. The elimination of these light and heavy components of the full boiling naphtha feed funnels or conditions the feed by reducing the variability of the extreme ends in the feed composition and by providing a light or heavy feed. However, as discussed elsewhere, while C11+'s should be removed, it is sometimes not desirable to remove the C10's by distillation, since the boiling points of some C8's and C9's are close to the boiling point of C10's, and removal of the C8's and C9's can be detrimental to the overall yield. Sometimes, however, in accordance with the flexibility feature of the invention, it may be desirable to remove all or most of the C10's, for example, where processing performance in downstream operations is less than adequate.

Preferably, the separation of the conditioned naphtha feed into a light reformer feed and a heavy reformer feed provides additional flexibility to divert selected components to either the monofunctional catalyst reformer or the bifunctional catalyst reformer, based on the naphtha feed characteristics. Preferably, if the naphtha feedstock contains a particularly high amount of C6 and C7 hydrocarbons, some of the C7 hydrocarbons are diverted to the bifunctional catalyst reformer. Conversely, when the naphtha feedstock contains a high amount of C8 and C9 hydrocarbons, some of the C8 hydrocarbons are preferably diverted to the monofunctional catalyst reformer.

Preferably, the monofunctional catalyst reformer has a catalyst in step (c) with the ability to handle very high paraffinic feeds. Paraffinic feeds typically require higher severity which increases the catalyst requirement and increases the coke-making tendency. Optionally, but preferably, the bifunctional catalyst reformer also has a catalyst in step (d) selected which can handle high paraffinic concentrations as well as high concentrations of naphthenic components in the feed. By overlapping the capabilities of both reformers to handle high concentrations of paraffin in the feed, the naphtha splitter can be operated to direct feed to whichever reformer is the least loaded with paraffins to maintain maximum aromatics production. Preferably, additional heater capacity may also be added to the monofunctional catalyst reformer or the bifunctional catalyst reformer, or both, to handle a higher naphthenic feed.

Preferably, the disproportionation step (f) above also provides for transalkylation of toluene and C9 aromatics. The overlapping capabilities of these two reactions provide not only disproportionation of toluene into mixed xylenes and benzene, but also for the transalkylation of toluene with C9 aromatics to produce more mixed xylenes. Preferably, the disproportionation reactor with transalkylation is designed to process an essentially pure toluene feed or a mixture of toluene and C9 aromatics, including up to and in excess of 50% by weight of C9 aromatics. Preferably, the disproportionation catalyst is tolerant of minor amounts of nonaromatics; e.g., 2–3% by weight paraffins in the feed, such that undesirable levels of catalyst fouling does not result. Optionally, but preferably, the ability to process a wide range of rates of C7 and C9 aromatics is further increased by varying the feed rate to the disproportionation reaction and by varying the run length between regenerations of the catalyst.

Figure 10:
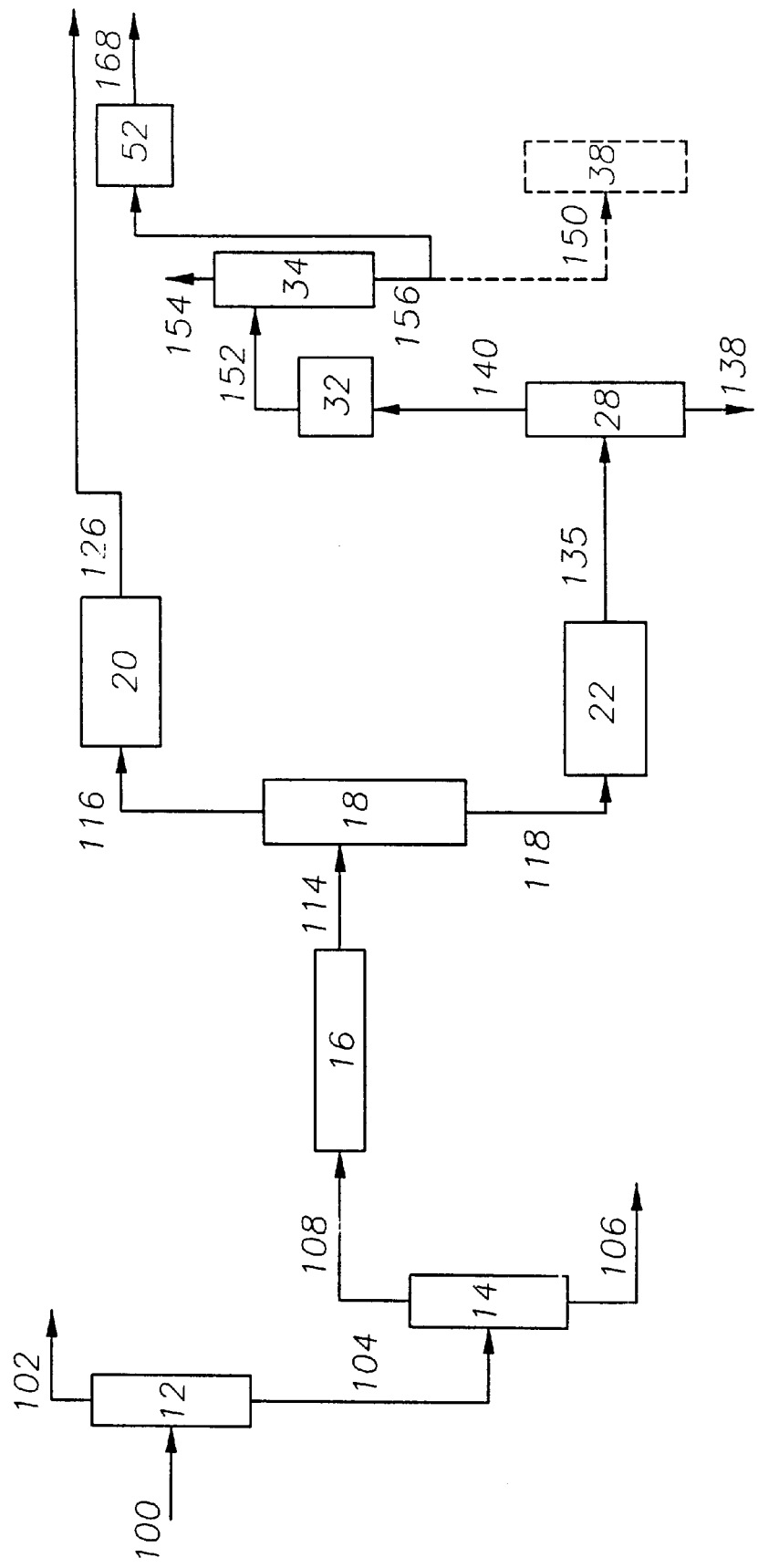
FIG. 10 is a block flow diagram of an alternate embodiment of the invention illustrating a method for processing a wide variety of feedstocks.

Referring to FIG. 10, and in connection with feed flexibility, a specific embodiment of the process includes removal of both light and heavy ends to provide high purity products from variable or fluctuating naphtha feedstock. In FIG. 10, the distillation of a purchased naphtha feed 100 in a depentanizer 12 provides an overhead product 102. Preferably, the overhead gas product 102 includes C5– hydrocarbons. However, the depentanizer column is designed with the overlapping capability to reject some or all of the C6 hydrocarbons along with the C5– hydrocarbons whenever the purchased naphtha feed 100 has a high benzene or high C6 to C7 hydrocarbon content Dimethylbutanes typically have a low yield rate for benzene production. Therefore, it is preferred that some or all of the dimethylbutanes present in the feed are rejected along with the C5– hydrocarbons. Optionally, additional C6 hydrocarbons, such as those components yielding a high rate of benzene, may be rejected whenever the processing capability of the aromatics complex is limited with respect to benzene. The bottoms product 104 from the distillation column 12 is fed to the heavy naphtha distillation column 14. This distillation step provides control over the heavy hydrocarbon content of the naphtha feed 108 by separating undesired heavy hydrocarbons from the naphtha feed 108, and removing the heavy hydrocarbons with the bottoms product, the heavy naphtha for storage 106. In combination, the control flexibility over the content of both the light and the heavy hydrocarbons in the naphtha feed 108 gained by the use of the depentanizer 12 and the heavy naphtha distillation column 14 give the processors the ability to maximize the recovery of the aromatics by funneling or diminishing the variability in the feed composition.

Optionally and preferably, the C10+ hydrocarbons are removed as part of the heavy ends naphtha for storage 106 by the heavy ends naphtha distillation column 14 when it is desired to concentrate xylenes in the feed. The removal of the heavier components increases the control flexibility to permit use of naphthas which may contain an undesirable quantity of C10+ components. These undesirable C10+ components can potentially harm the downstream processing unit in the aromatics complex. Removal of these undesirable C10+ or heavy components is therefore desirable.

The overhead product 108 (the "naphtha feed") from the heavy naphtha distillation column 14 is fed to a naphtha hydrotreater 16. The hydrotreated naphtha 114 is distilled in the naphtha splitter 18 to provide a light reformer feed 116 and a heavy reformer feed 118. The distillation performed in the naphtha splitter 18 allows the processors to divert selected hydrocarbon components to either the monofunctional catalyst reformer 20 or the bifunctional catalyst reformer 22. Preferably, the naphtha splitter 18 makes a sharp-cut separation between the C8+ hydrocarbons and the C7– hydrocarbons such that the heavy fraction has little or no C7's and the light fraction has little or no C8+'s. Preferably, the heavy reformer feed 118 has less than about 10% by liquid volume of C7's and the light reformer feed 116 has less than about 5% by liquid volume of C8's. Optionally, and preferably, if the naphtha feedstock contains a particularly high amount of C6 and C7 hydrocarbons, such that the monofunctional catalyst reformer 20 is at too high a load, the C7 hydrocarbons are diverted by the naphtha splitter 18 into the bottoms product 118 (the "heavy reformer feed"). The diversion of the C7 hydrocarbons from the monofunctional catalyst reformer 20 and into the bifunctional catalyst reformer 22 provides for an increase of the aromatics yield by maximizing the actual feed rate through the entire aromatics complex.

Optionally, but preferably, C9 hydrocarbon handling capability is augmented by increasing the amount of C9's ultimately fed to the disproportionation unit 52. This is accomplished by maintaining the C9's in the heavy reformer feed 118 at a relatively high level and feeding them to the bifunctional catalyst reformer 22. The heavy reformate 135 from the bifunctional catalyst reformer 22 is then fed to the reformate splitter 28. The overhead product 140 (the "third benzene-rich stream") is fed to the extractive distillation column 32.

The extract 152 from the extractive distillation column 32 is fed to the benzene recovery column 34. An overhead product 154 (the "high purity benzene product") is distilled in the benzene recovery column 34. The bottoms product 156 from the benzene recovery column 34 is fed to the disproportionation reaction 52. Preferably, the disproportionation reactor 52 also provides for transalkylation of toluene and C9 aromatics. The overlapping capabilities of these two reactions not only provide for disproportionation of toluene into mixed xylenes and benzene, but also for the transalkylation of toluene and C9 aromatics to produce more mixed xylenes. Preferably, the disproportionation/transalkylation reaction catalyst has the overlapping capability to handle anywhere from a high purity toluene feed to a mixed feed that is roughly 50% by weight toluene and C9 aromatics.

D. Disproportionation of Unextracted Toluene

According to another alternate embodiment of the present invention, a process for making high purity benzene and high purity paraxylene includes the step of subjecting an unextracted toluene-rich aromatics stream to a disproportionation step where the aromatics stream also contains minor amounts of nonaromatics, e.g., up to about 5.0% paraffins that co-boil with toluene.

Among other factors, this embodiment of our invention is based on the finding that the non-acidic catalyst used for the light reformer feed converts C7 paraffins faster than C6 paraffins. Thus, when the plant conditions are optimized to maximize benzene conversion, very little unreacted C7 and C8 paraffins remain. As a result, extraction of the toluene stream to remove nonaromatics from the toluene stream before disproportionation is no longer required. This surprisingly high purity benzene product may be made even when the unextracted toluene contains about 2–3% paraffins by weight that co-boil with the toluene.

Optionally, and preferably, the disproportionation step includes transalkylation reactions. The combination of transalkylation reaction facilitates use of variable feedstocks. If a feedstock is rich in C8–C9 hydrocarbons, C9 hydrocarbons may be directed to the disproportionation step. Conversely, the disproportionation step may process an essentially pure toluene feed.

Another aspect of the invention is directed to distilling the monofunctional reformate stream in a common distillation train with the disproportionation effluent. Preferably, the first column in the common distillation train has separate feed locations for the unstabilized reformate and disproportionation effluent so that both may be distilled in a common distillation column. Where each stream is fed separately to the column, the feed tray locations for each stream should be based upon approximately matching the internal composition profile of the distillation column. More specifically, this alternate embodiment of the invention preferably includes the steps of: (a) reforming at least one hydrocarbon feed stream to provide a first product stream, which has an aromatics component comprising benzene, toluene and xylene, and a non-aromatics component comprising paraffins (preferably no more than about 3% by weight paraffins that co-boil with toluene); (b) separating the first product stream into a toluene-rich stream and a xylene-rich stream (e.g., via a T/X splitter); (c) subjecting the unextracted toluene-rich stream (which still has a certain level of non-aromatics, e.g., as much as 3% by weight paraffins that co-boil with toluene) to disproportionation, to provide a mixed aromatics stream (benzene, toluene and xylene); (d) stabilizing the mixed aromatics stream of step (c) with the first product stream of step (a) to remove light ends; and (e) separating the stream of step (d) into a benzene-rich stream and a benzene-lean stream.

Optionally, in one aspect of the invention, the mixed aromatics stream (from step (c)) may be stabilized to remove light ends. In another aspect, the mixed aromatic product stream may be separated (e.g., via a B/T splitter) into a benzene-rich stream and a toluene-rich, or optionally, a C7+ stream, after which the benzene-rich stream may be subjected to aromatics extraction to remove nonaromatics, and to provide a high-purity benzene product stream. Other specific embodiments of the invention may include incorporating a split feed feature (with monofunctional and bifunctional reforming) and recovery of high-purity benzene and high-purity paraxylene.

Among other factors, this embodiment of our invention is based on our finding that the non-acidic catalyst used for the light reformer feed converts C7 paraffins faster than it converts C6 paraffins. Thus, when the plant conditions are optimized to maximize benzene conversion, very little unreacted C7 and C8 paraffins should remain. As a result, extraction of the toluene stream to remove non-aromatics from the toluene stream before disproportionation is preferably no longer required. The light reformate contains a small amount of toluene co-boiling nonaromatics, preferably in the range of about 0.2 to 5.0% by weight. Optionally and preferably, an acidic paraxylene selective disproportionation catalyst that is tolerant to high concentrations of paraffin is used. Specific embodiments of this aspect of the inventions are disclosed in U.S. patent application Ser. No. 07/952,312 which is hereby incorporated to the extent it is not inconsistent with the present invention. Preferably, the disproportionation steps and recycle loops in the integrated process are utilized in the present invention to convert substantially all of the toluene to benzene and paraxylene. As no or very little toluene product is produced, no toluene product specifications for nonaromatic content need be met. Therefore, as no toluene product specifications need to be met along with the discovery of the paraffin tolerant disproportionation catalyst, no extraction of the toluene containing streams is required. Optionally, other feedstocks rich in C7+ hydrocarbons may be processed in the disproportionation step. Optionally, the disproportionation step may include transalkylation such that up to about 50% by weight of the disproportionation step feed contains C9 aromatics.

Figure 3:
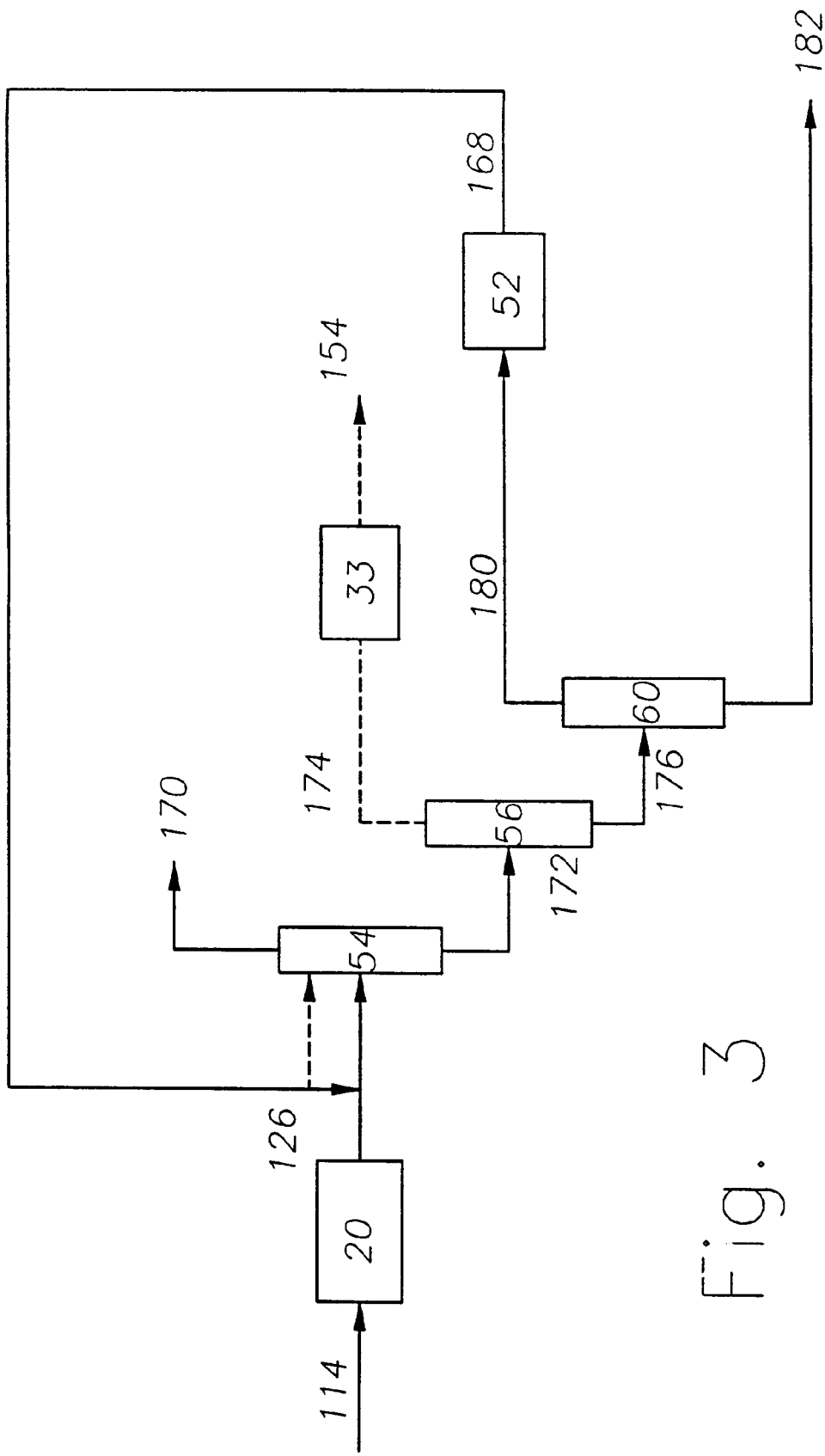
FIG. 3 is a block flow diagram of an alternate embodiment of the invention illustrating the disproportionation of unextracted toluene.

Referring to FIG. 3, a process for making high purity benzene and high purity paraxylene involving the disproportionation of unextracted toluene will be described. The hydrocarbon feed 114 may be reformed using either a monofunctional catalyst or a bifunctional catalyst in a reformer 20 to provide one or more reformate streams 126. The reformate stream 126 may be separated in a stabilizer column 54 to provide a stabilized bottoms product 172 and to remove any C5– hydrocarbons as light ends 170. The light ends 170 may preferably be sent to fuel gas. The stabilized bottoms product 172 from the stabilizer column 54 may be fed to a B/T splitter 56 where it is fractionated into a first benzene-rich stream 174. Optionally, but preferably, the first benzene-rich stream 174 is sent to the benzene finishing steps 33. Preferably, the benzene finishing steps 33 may include extraction or distillation or both. The benzene finishing steps 33 preferably provide a high purity benzene stream 154. The B/T splitter bottoms product 176, (the "first toluene-rich stream"), may be fed to the T/X splitter 60 where it is separated into a second toluene-rich stream 180 which may be fed to the disproportionation reactor 52 and a first xylene-rich stream 182. The disproportionation reaction effluent 168 may be recycled to the stabilizer column 54.

E. Restricted Heat Integration

In another alternate embodiment of the present invention, a process for making high purity benzene and high purity paraxylene involves applying use of an indirect heat exchange system or "restricted" heat integration. Advantageously, the method uses shell and tube exchangers to heat a reboiler liquid from one distillation column by condensing the overhead vapors from another distillation column. As used herein, the term "heat integration" refers to using a distilled process stream, e.g., overhead vapors or reboiler liquid, as a heat source or sink, respectively, for another distilled process stream from another distillation column.

The process for making benzene and paraxylene may include sequential distillations of various hydrocarbon streams, each having different concentrations of benzene, toluene and xylenes. In accordance with the heat integration aspect of the invention, shell and tube exchangers heat a reboiler liquid from one distillation column by condensing the overhead vapors from another distillation column. More preferably, the overhead vapors of one distillation column in the aromatics complex flow through the shell side of the heat exchanger, and when condensing, the vapors release the latent heat of vaporization in order to indirectly reboil the reboiler liquid of another column in the aromatics complex, wherein the reboiler liquid flows through the shell side of the heat exchanger.

Among other factors, in accordance with the invention, it has been discovered that control flexibility to meet distillation specifications may be maintained if the heat integration in a distillation train is restricted such that a portion of the heat available from the condensing vapors is rejected to an external heat sink such as cooling water or steam generation. For example, in a specific embodiment, at least about 5% or 10% of the available heat is made rejected in such a manner. Alternatively, the amount of heat can be as much as about 15% or even 20%. This restriction facilitates sufficient heating for unusual or upset conditions such as a sudden increase in feed rate that may suddenly increase heating requirements of the reboiler liquid. Conversely, by designing the integration to include an external heat sink, sudden decreases in the heating requirements may also be robustly controlled. By limiting the condenser duty in this manner, the reboiled liquid duty may be fully supplied by the external overhead vapors of the integrated column to further promote controllability. Additionally, heat integration may be restricted so that only the condenser or reboiler of any one distillation column is integrated to further promote controllability and responsiveness of any distillation steps using restricted heat integration.

Optionally, and preferably, further controllability may be maintained if the heat integration is restricted to either the condenser or reboiler. By further restricting the heat integration to one end of the distillation column, e.g., the condenser or reboiler end of the column, the unintegrated or free end of the distillation column will use an external heat sink or source, e.g., cooling water, steam generation, fans, hot oil, process heaters, and the like. This lessens the thermal coupling to other columns and gives further stability to the heat integration.

By limiting the heat integration to either the condenser or reboiler, process upsets or variability may be dampened by conventional sources of heating or cooling used at the remaining end of the column. In accordance with this aspect of the present invention, the heat sources, e.g., condensing vapors, and heat needs, e.g., reboiling hydrocarbon liquids, may be arranged to conserve energy without sacrificing control objectives or distillation product specifications.

Additionally, typical aromatics complexes often employ technology from outside sources. A particular technology source may develop an optimized heat integration scheme for any required distillation within the scope of that work. This approach results in a local optimization, e.g., optimized for only the sources and sinks within the scope of that licensor's work, without consideration for the global or overall aromatics complex heat sources and needs. In a specific embodiment of the present invention, the heating and cooling needs for the overall complex distillation requirements are integrated such that only one end of a column is heat integrated with another column. In addition, by combining streams from individual technology source areas into common streams for distillation so that capital costs and operating costs may be reduced by the integration of the heat sources and heat needs.

For example, in a specific embodiment of the invention that includes heat integration, the process may include: (a) distilling a combined stream in a first distillation column, said combined stream comprising imported reformate or mixed xylenes and stabilized reformate from a conventional reformer, to provide an overhead C7− fraction and a bottoms C8+ fraction, said distillation including a reboiling step; and (b) distilling the C8+ fraction of step (a) in a second distillation column to provide an overhead C8 vapor fraction for subsequent paraxylene recovery and a C9+ fraction, wherein prior to paraxylene recovery the overhead C8 vapor makes heat exchange contact with the reboiler liquid of step (a) such that the overhead C8 vapor is condensed to form a high temperature C8 liquid.

Other specific embodiments of the invention may involve additional distillation steps, where certain overhead vapor streams are directed to make heat exchange contact with certain reboiler liquid streams, such that the vapor streams are condensed to form high temperature liquid streams, and the temperatures of the reboiler liquid streams are increased.

For example, the process may include a distillation of an aromatic-containing extract from the adsorber. This distillation results in a C6–C7 fraction (the "light product stream"), a paraxylene-deficient C8 fraction (the "first internal recycle") and a paraxylene-rich C8 fraction (the "second paraxylene-rich stream"), the latter being subsequently subjected to crystallization into a high purity paraxylene product, includes use of a reboiler, wherein heat to that reboiler is provided by making heat exchange contact with overhead vapors (the "second internal recycle") from a raffinate distillation column and condensing the overhead vapors (the "second internal recycle"). Similarly, the distillation of an isomerization effluent column containing mixed xylenes, benzene and toluene provides a C8+ fraction and a benzene-rich fraction for subsequent extraction. This distillation includes a reboiling step, and the reboiler liquid is heated by making heat exchange contact with the C8 vapor fraction from the distillation of step (b) above.

Referring to FIGS. 4a–4d, several specific embodiments of the process of the present invention are illustrated using an indirect heat exchange system. Five separate heat integrations provide that overhead vapors from particular columns supply reboiled duties to other distillation columns.

Figure 4B:
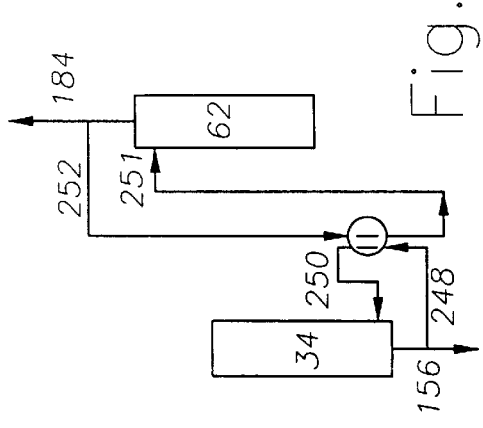
FIG. 4b is a block flow diagram of an alternate embodiment of the invention illustrating an indirect heat exchange system between the heavy gasoline splitter and the benzene recovery column.
Figure 4D:
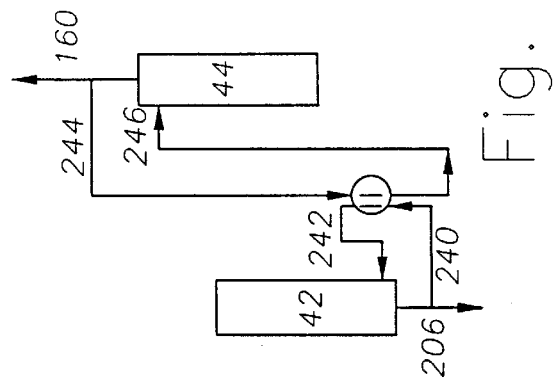
FIG. 4d is a block flow diagram of an alternate embodiment of the invention illustrating an indirect heat exchange system between the extract column and the raffinate column.
Figure 4A:
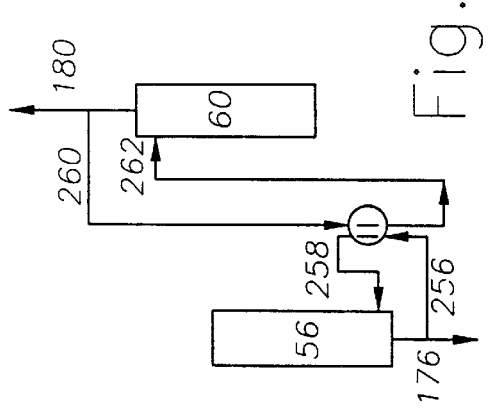
FIG. 4a is a block flow diagram of an alternate embodiment of the invention illustrating an indirect heat exchange system between the B/T splitter and the T/X splitter.

Referring to FIG. 4a, the first heat integration of the present invention occurs between the B/T splitter 56 and the T/X splitter 60. A portion 256 (the "first reboiler stream") withdrawn from the splitter bottoms product 176 (the "first toluene-rich stream") is reboiled by indirect heat exchange contact in a heat exchanger with a portion 260 (the "first condensing stream") of the overhead stream 180 (the "second toluene-rich stream"), which reboils the first reboiler stream 256 as it condenses and gives up the latent heat of vaporization. Optionally, subcooling occurs. Following the heat exchange between the first reboiler stream 256 and the first condensing stream 260, the reboiled liquid 258 (the "first reboiled stream") is returned to the B/T splitter 56 and the condensed vapors 262 (the "first condensed stream") are returned to the T/X splitter 60.

Referring to FIG. 4b, a second heat integration occurs between the heavy gasoline splitter 62 and the benzene recovery column 34. A portion 248 (the "second reboiler stream") of the bottoms product 156 from the benzene recovery column 34 is withdrawn as the second reboiler stream 248. The second reboiler stream 248 is used to condense a portion 252 (the "second condensing stream") of the light aromatic stream overhead 184 from the heavy gasoline splitter 62 as the second condensing stream 252. The second reboiled stream 250 is returned to the benzene recovery column 34. The second condensed stream 254 is returned to the heavy gasoline splitter 62.

Figure 4C:
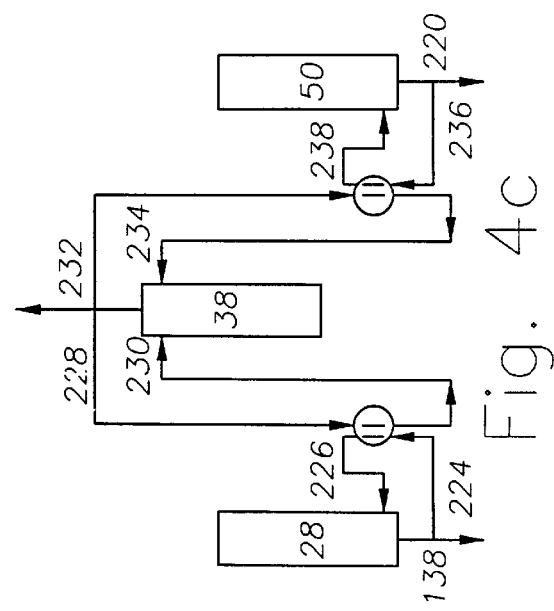
FIG. 4c is a block flow diagram of an alternate embodiment of the invention illustrating an indirect heat exchange system between the xylene rerun column and the reformate splitter and between the xylene rerun column and the light aromatics stabilizer.

Referring to FIG. 4c, a third heat integration occurs between the xylene rerun column 38 and the reformate splitter 28. A portion 224 (the "third reboiler stream") of the bottoms product 138 (the "second xylene-rich stream") from the reformate splitter 28 is used to condense a portion 228 (the "third condensing stream") of the overhead vapors 194 (the third xylene-rich stream") from the xylene rerun column 38. The portion withdrawn from the bottoms product 138 to be reboiled, the third reboiler stream 224 indirectly contacts the third condensing stream 228 to simultaneously reboil and condense the respective streams. The third reboiled stream 226 is returned to the reformate splitter 28 and the condensed vapors 230 (the "third condensed stream") are returned to the xylene rerun column 38.

Again referring to FIG. 4c, the fourth heat integration occurs between the light aromatics stabilizer column 50 and the xylene rerun column 38. A portion 236 (the "fourth reboiler stream") of the bottoms product 220 (the "fourth xylene-rich stream") is used to condense the portion 232 (the "fourth condensing stream") of the overhead vapors 194 (the "third xylene-rich stream") from the xylene rerun column 38. The fourth reboiler stream 236 is indirectly contacted with the fourth condensing stream 232. Following indirect heat contact, the reboiled liquid 238 (the "fourth reboiled stream") is returned to the light aromatics stabilizer column 50 and the condensed overhead vapors 234 (the "fourth condensed stream") are returned to the xylene rerun column 38.

Referring to FIG. 4d, a fifth heat integration occurs between the extract column 42 and the raffinate column 44 within the adsorber unit. A portion 240 (the "fifth reboiler stream") of the bottoms product 206 (the "second paraxylene-rich stream") from the extract column 42 is used to condense a portion 244 (the "fifth condensing stream") of the overhead vapors 160 (the "light product stream") from the raffinate column 44. A portion 240 (the "fifth reboiler stream") of the bottoms product 206 (the "second paraxylene-rich stream") to be reboiled is indirectly heated by a portion 244 (the "fifth condensing stream") of the light product stream 160 from the raffinate column 44. Following the indirect heat exchange, the reboiled liquid 242 (the "fifth reboiled stream") is returned to the extract column 42. The condensed vapors 246 (the "fifth condensed stream") are returned to the raffinate column 44.

F. High Purity Benzene Production with Selective Feed Cutting

According to still another embodiment of the invention, a process is provided for making high purity benzene and high purity paraxylene that includes steps for purifying and finishing the benzene product to an extremely high purity, preferably to at least about 99.989% by weight benzene. This alternate embodiment includes the following steps: (a) clay treating; (b) selective hydrogenation; (c) extraction; and (d) distillation. The first treatment step (a) may be used optionally on intermediate streams, i.e., before or after fractionation of any benzene rich streams. The surprisingly high purity of the benzene produced by this embodiment of the invention exceeds the ASTM Refined Benzene-545 standard having a toluene concentration of about 40 ppm by weight or less and a non-aromatics concentration of about 70 ppm or less by weight Preferably, produced benzene streams are clay treated to partially remove olefins. Optionally, but preferably, streams with low olefin content bypass the clay treaters to minimize aromatics losses and decrease processing requirements. Preferably, the heavy reformate, including any produced benzene, is clay treated after stabilization to partially remove olefins. Effluent from the disproportionation step is also preferably clay treated after stabilization to partially remove olefins. More preferably, the disproportionation effluent is clay-treated following fractionation and removal of the benzene-rich stream. Optionally, but also preferably, produced benzene from the light reformate is bypassed around clay treatment.

The conditions for adsorbing or removing olefins or other undesirable compounds may include temperature of about 100° C. to 300° C., preferably 160° C. to 230° C.; and hourly space velocities of about 1 to 8, preferably 1 to 4; and pressure of about 3 to 100 bar, preferably 4 to 20 bar. The type of clay used in the present invention may be an activated natural aluminosilicate, for example, the clay referenced as F54 available from Engelhard Industries, Inc.

In order to hydrogenate diolefins and partially hydrogenate olefins from the benzene product, the combined benzene-rich streams may be selectively hydrogenated. Optionally, but preferably, the feed stream to the selective hydrogenation step (b) includes a benzene-rich stream distilled from an isomerization effluent, if any. The clay treated benzene-rich stream fractionated from the heavy reformate may be bypassed around the selective hydrogenation step.

Figure 6:
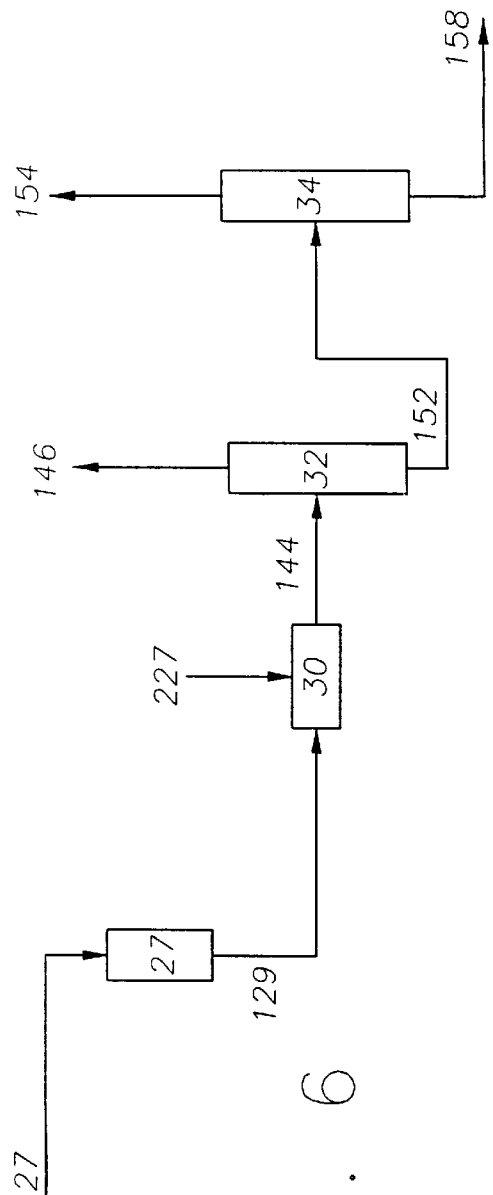
FIG. 6 is a block flow diagram of an alternate embodiment of the invention illustrating benzene finishing.
Figure 5:
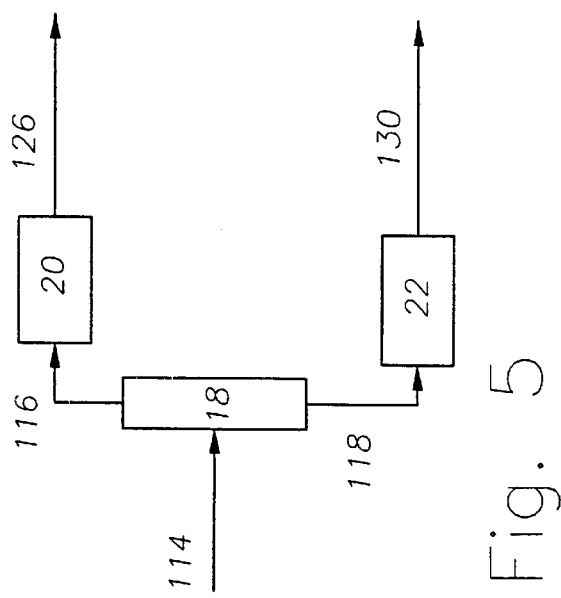
FIG. 5 is a block flow diagram of an alternate embodiment of the invention illustrating high octane reforming.

Referring to FIG. 6, a specific embodiment of the present invention is a process for making high purity benzene and high purity paraxylene that includes benzene finishing. The method of this embodiment includes clay treating 27 one or more combined benzene-rich streams 127 to provide a clay-treated stream 129 to decrease olefin concentration. The clay-treated stream is then fed along with a hydrogen stream 227 to a selective hydrogenation reactor 30 to hydrogenate diolefins and partially hydrogenate olefins. The selective hydrogenation effluent 144 is fed to an extractive distillation column 32 to remove non-aromatics. The extract 152 is fed to the benzene recovery column 34 where the extract 152 is separated into a high purity benzene stream 154 and a bottoms product 158.

G. Internally Produced Toluene Desorbent

In another alternate embodiment of this invention, a process for purifying paraxylene includes the following steps: (a) providing internally produced toluene to the desorption section of a simulated moving bed adsorber that includes a solid adsorbent; (b) desorbing with the internally produced toluene, a selectively adsorbed product, preferably paraxylene, from the solid adsorbent; (c) collecting an extract comprising the internally produced toluene and paraxylene and a raffinate containing the internally produced toluene and other C8 isomers; and (d) distilling the extract and raffinate to recover a substantial amount of desorbent for recycle to the simulated moving bed adsorber.

Methods for the production of paraxylene typically include xylene separation processes in conjunction with isomerization processes. A C8 aromatics mixture containing xylene isomers and ethylbenzene may be separated using a simulated moving bed liquid chromatography method to provide a paraxylene-rich stream and a paraxylene-deficient stream. To produce both of these streams, a desorbent is required. Preferably, the desorbent is one that is relatively easily separated from the paraxylene and the other isomers without causing purity problems for the finished paraxylene product or conversion problems for the isomerization unit, or both.

Among other factors, this specific embodiment is based on our findings that sufficient toluene may be produced by the aromatics complex such that it may be distilled and separated from both the raffinate and extract products from the adsorber to provide the required desorbent for internal use by the adsorber. Toluene is separated by distillation from both the paraxylene and the other isomers of paraxylene. Preferably, the distillation of the extract and the raffinate results in small losses of desorbent which may be recovered from the internal sources described above. Because make-up toluene may be internally produced, the distillation of the raffinate and the extract may leave residual amounts of toluene in these streams, such that xylene losses to the desorbent are reduced. Optionally, but also preferably, the distillation of the raffinate results in small losses of the less preferably adsorbed components, e.g., orthoxylene and metaxylene. Furthermore, the internally produced toluene does not exhibit build-up problems in the recycle streams as does diethylbenzene. Nor do purity problems result with the final paraxylene product when using toluene as a desorbent Preferably, any excess toluene not needed as a desorbent is stored. More preferably, excess toluene is fed to a disproportionation unit to produce more benzene and paraxylene. Alternately, any deficiency in toluene needed as a desorbent is internally sourced from the bottoms product of the benzene recovery column.

Figure 7:
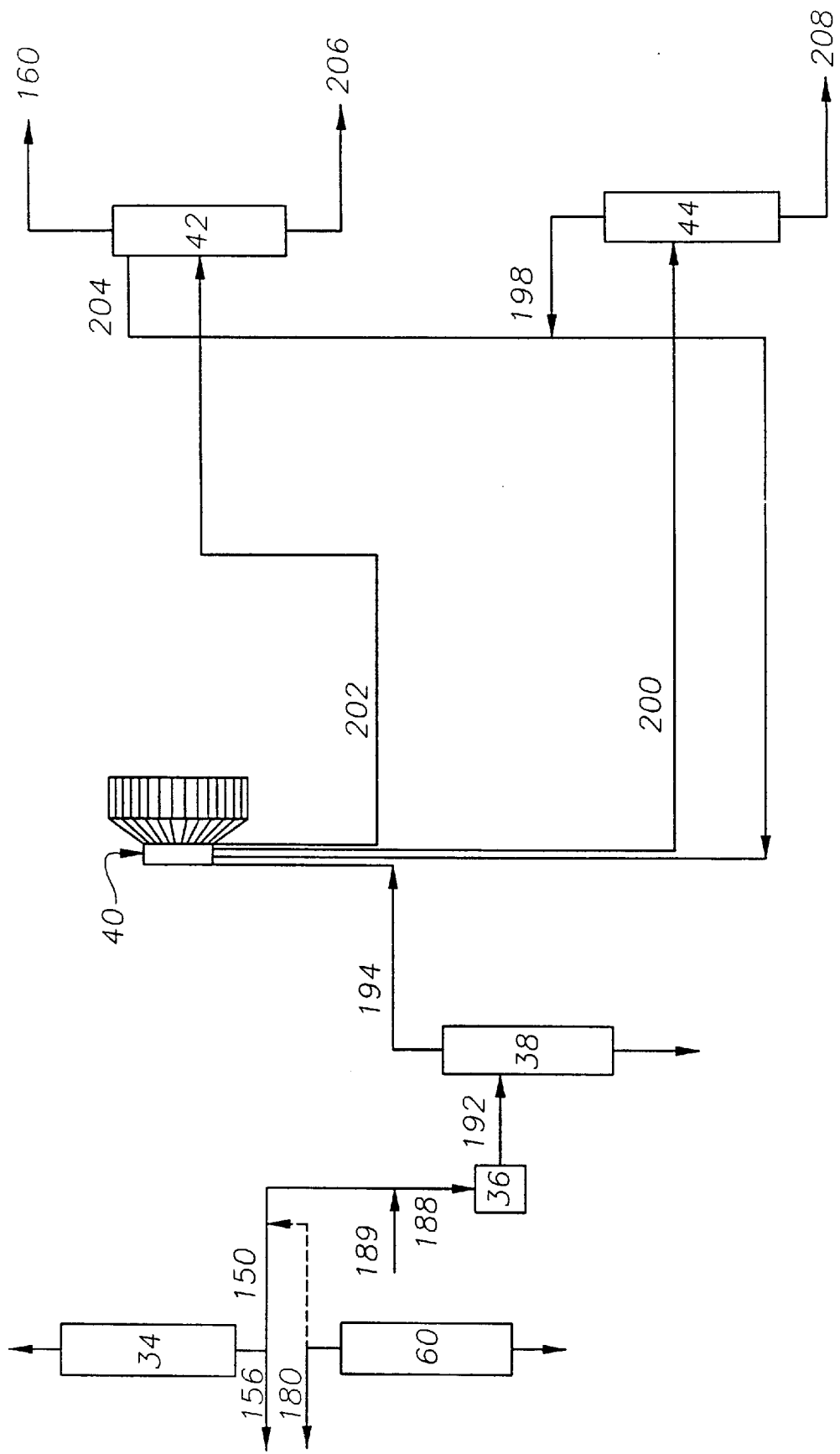
FIG. 7 is a block flow diagram of an alternate embodiment of the invention illustrating the use of internally produced toluene as a desorbent.

Referring to FIG. 7, a specific embodiment of the present invention is a process to produce high purity benzene and high purity paraxylene that includes internal production of a toluene adsorbent. Toluene desorbent make-up 150 is preferably sourced from the benzene recovery column 34 bottoms product 156. Alternately, it may be sourced from the overhead of the T/X splitter 60, the second toluene-rich stream 180. The toluene desorbent make-up 150 may then be combined with a xylene-rich stream 189 (the "fifth xylene-rich stream") to form another xylene-rich stream 188 (the "sixth xylene-rich stream"). The sixth xylene-rich stream may then be clay treated 36 and fed to the xylene rerun column 38. The overhead from the xylene rerun column 194 (the "third xylene-rich stream") may then be fed to an adsorber 40. Preferably, the adsorber 40 is a countercurrent unit which may use a zeolitic adsorbent which exhibits a strong affinity or selectivity for paraxylene. In this preferred embodiment, the adsorber 40 sequentially opens and closes different feed and product ports to simulate the movement of an adsorbent bed past liquid inlet ports 43 and outlet ports 45. The adsorbed paraxylene-rich product 202 (the "first paraxylene-rich stream") from the simulated moving bed is fed to an extract column 42. A side-stream product 204 (the "first internal recycle") distilled in the extract column 42 is separated and recycled to the adsorber 40. A light product stream 160 is taken overhead from the extract column 42 and may be recycled to a disproportionation reactor to increase aromatic yields. The bottoms product 206 (the "second paraxylene-rich stream") is fed to crystallization. A raffinate product 200 from the adsorber 40 is fractionated in the raffinate column 44. The desorbent 198 (the "second internal recycle") is distilled overhead in the raffinate column 44 and may be recycled to the adsorber 40. The first paraxylene-deficient stream 208, the distilled bottoms product from the raffinate column 44, may be fed to an isomerization reactor.

H. Paraxylene Recovery

Yet another alternate embodiment of the invention includes a process for purifying and finishing the paraxylene product to a surprisingly high purity, preferably to about 99.9% by weight paraxylene. The process may include separating paraxylene from other C8 aromatics, including orthoxylene, metaxylene and ethylbenzene. The process preferably includes one or more of the following steps: (a) separating a xylene-rich stream into a paraxylene-rich stream and a paraxylene-deficient stream by simulated moving bed adsorption; and (b) crystallizing the first paraxylene-rich stream to produce a high purity paraxylene product.

Among other factors, this embodiment of the present invention is based on our finding that the purity of a paraxylene product is increased unexpectedly by using a combination or "hybrid" of processing steps. Generally, crystalline product purities range from about 99.5% to 99.8% by weight. To increase the purity beyond this range, occlusions caused by small pockets of mother liquor trapped within the crystals are partially eliminated or the impurities in the trapped mother liquor reduced. Lower levels of impurities in the mother liquor or better washing of the crystals, or both, tends to improve product purity.

In particular, the combination or "hybrid" of processing steps includes adsorption, preferably simulated moving bed adsorption, followed by one or more stages of crystallization. Preferably, a countercurrent simulated moving bed adsorption yielding an intermediate purity of about 80% to about 98% by weight paraxylene is used. More preferably, a countercurrent simulated moving bed adsorption yielding an intermediate purity of about 90% to about 98% by weight paraxylene is used in conjunction with either a single or double stage crystallization. In a specific embodiment of the invention, the purification step (a) uses an internally produced toluene as the desorbent, e.g., a toluene stream produced by the system of this invention.

The crystallizing step (b) above preferably comprises two high temperature crystallization stages with internal mother liquor recycles. More preferably, one high temperature crystallization stage is used. The crystallization zone temperature is preferably high, e.g., between about −10 and +25° C. as described in MacPherson U.S. application Ser. No. 08/875,278. Excess mother liquor is preferably recycled to the xylene rerun column via a clay treater. Preferably, the recovered crystals are washed in at least one separation and washing zone, to provide paraxylene product along with a byproduct or "rejected" stream that includes impurities removed from around the paraxylene crystals that were formed in the crystallization step and also includes some paraxylene.

Referring to FIG. 8, a process for making high purity benzene and high purity paraxylene includes a method to recover and finish paraxylene. The method to recover and finish paraxylene of the present invention includes feeding a xylene-rich stream 194 (the "third xylene-rich stream") to an adsorber 40. Preferably, the adsorber 40 employs a zeolitic adsorbent which exhibits a strong affinity or selectivity for paraxylene. In this preferred embodiment, the adsorber 40 uses countercurrent adsorption techniques, including use of a valve manifold 41 which sequentially opens and closes different feed and product ports simulating the movement of adsorbent bed past fixed liquid inlet ports 43 and outlet ports 45. The adsorbed paraxylene-rich product 203 is fed to a crystallization unit 48. The crystals produced in the crystallization unit 48 are filtered and washed in a separation and washing zone. Preferably, the wash liquid 205 is paraxylene, but other solvents such as toluene may be used. When washing with paraxylene, the resulting high purity paraxylene 214 preferably has a 99.9% by weight purity. Optionally, the crystallization unit 48 has two or more stages. However, one stage of crystallization may be used. Preferably, mother liquor 207 from the crystallization unit 48 is internally recycled inside the crystallization unit 48 or recycled to a xylene rerun column.

As discussed in the background, the process disclosed by MacPherson in U.S. application Ser. No. 08/875,278 discloses a method for recovering high purity paraxylene. That process scheme may be used advantageously in the present invention. In particular, a stream rich in mixed xylenes is subjected to crystallization in a crystallization zone. The crystals are separated from the mother liquor in a separation zone and washed in a separation zone, e.g., a wash column with a paraxylene or non-paraxylene absorbent, e.g., toluene, resulting in a paraxylene-rich "washing liquor" or filtrate. Prior to washing, however, the crystals are directed to a reslurry tank (referred to therein as a "partial melting zone") where the crystals are contacted in a mixing vessel with a recycled portion of the paraxylene-rich washing liquor from the wash column. Preferably, the crystals that are treated in the reslurry tank include small quantities of residual mother liquor, e.g., 2 wt %. The paraxylene concentration of paraxylene in the recycled washing liquor from the wash column can be higher than the paraxylene concentration in the mother liquor. Preferably, the paraxylene crystals from the initial crystallization are subjected to a reslurry step, e.g., in a reslurry tank, then to a purification and washing step. Preferably, in the reslurry step, the paraxylene crystals are mixed with a recycle stream of filtrate or mother liquor from the purification and washing step. This recycle stream contains the impurities that are removed in the purification and washing step, and also contains some paraxylene. Accordingly, the net result is that the paraxylene concentration of the crystalline product is increased, preferably to a purity of 99.9 wt % paraxylene.

I. Processing Unstabilized Light Aromatics Directly to Extraction

Still another alternate embodiment of the invention for making high purity benzene and high purity paraxylene includes a method for processing unstabilized light aromatics. Preferably, the process includes the following steps: (a) hydrogenating a benzene-rich hydrocarbon stream comprising an unstabilized isomerate to hydrogenate diolefins and partially hydrogenate olefins; and (b)extracting the product of step (a) to remove non-aromatics.

Among other factors, this specific embodiment of the invention is based on our finding that the light aromatic fraction of the isomerate comprising unstabilized benzene and toluene may be extracted directly where the process includes stabilization, e.g., removal of light hydrocarbons, such as C1–C5 hydrocarbons. The light hydrocarbons can include the effluents from the catalytic reforming step, using either a monofunctional catalyst or a bifunctional catalyst, or both, and a disproportionation step. By stabilizing or removing the light hydrocarbons, e.g., the C1–C5 hydrocarbons, from these combined streams, the isomerization effluent may be extracted without being stabilized while reducing losses of hydrocarbons to the fuel gas system or flare.

Referring to FIG. 9, a specific embodiment of the process of the present invention to produce high purity benzene and high purity paraxylene includes a method of processing unstabilized light aromatics directly to extraction. This method for processing unstabilized light aromatics includes hydrogenating a benzene-rich hydrocarbon stream 219 with hydrogen 227 in a selective hydrogenation reactor 30 to hydrogenate diolefins and partially hydrogenate olefins to purify the benzene in order to exceed the ASTM Refined Benzene-545 standard. Preferably, the benzene-rich stream 219 includes the first benzene-rich stream 174 distilled overhead by the B/T splitter 56 and the second benzene-rich stream 222 distilled from the isomerate effluent 218 in the light aromatics stabilizer column 50. The selective hydrogenation reaction effluent 144 may be extractively distilled in an extractive distillation column 32 to provide a raffinate product 146 and an extract 152 that is rich in benzene.

J. Common Distillation for Monofunctional Reformate and Disproportionation Effluent An alternate embodiment of the present invention for making high purity benzene and high purity paraxylene includes a process for fractionating, preferably in a single distillation train, a monofunctional reformate and an effluent from disproportionation into narrower boiling components for product recovery and finishing or further processing. Preferably, this specific embodiment includes one or more of the following steps: (a) distilling an unstabilized monofunctional reformate and an unstabilized disproportionation effluent in a common fractionator into a bottoms liquid stream and overhead gas stream; (b) distilling the bottoms liquid stream of step (a) to provide a benzene-rich overhead stream and a bottoms stream; and (c) distilling the bottoms stream of step (b) into a toluene-rich overhead stream and a xylene-rich stream.

Among other factors, this specific embodiment of the present invention is based on our findings that the compositions of the unstabilized monofunctional reformate and unstabilized disproportionation effluent are sufficiently similar so that they may be combined and processed in a common distillation train. The unstabilized reformate and disproportionation effluent may be combined and fed to a stabilizer column to remove light ends (C5–) hydrocarbons. Preferably, the first column in the common distillation train has separate feed locations for the unstabilized reformate and unstabilized disproportionation effluent so that they may be distilled in a common distillation column, but fed separately to the column based upon matching the feed with the internal composition profile inside the distillation column. Optionally, the feed to the disproportionation reactor is also fed to the stabilizer tower.

Optionally, but preferably, the disproportionation feed contains C9 hydrocarbons which are transalkylated to increase benzene and paraxylene yield in the disproportionation effluent in step (a). Optionally, but preferably, in the first distillation step (a) the entrance location of the monofunctional reformate and the disproportionation effluent are configured separately to closely match the internal composition profile. Preferably, before the distillation of step (b), the bottoms liquid product is clay treated to partially remove olefins. More preferably, clay treating is performed after the distillation of step (b). In step (c), the overhead toluene-rich stream is preferably recycled, more preferably without extraction, to the disproportionation reaction to decrease overall processing requirements of the extraction step.

Figure 11:
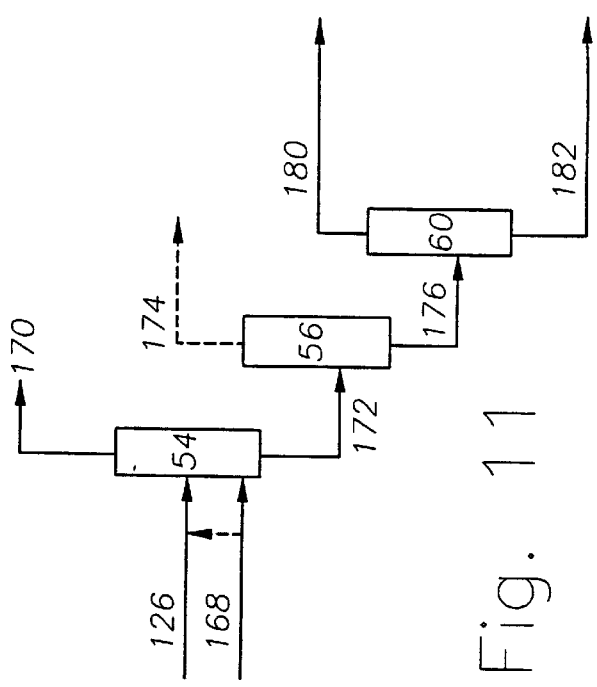
FIG. 11 is a block flow diagram of an alternate embodiment of the invention illustrating a method of processing the monofunctional reformate and disproportionation effluent in a single distillation train.

Referring to FIG. 11, a specific embodiment of the process of the present invention to make high purity benzene and high purity paraxylene includes the step of fractionating in a single distillation train a monofunctional reformate 126 and a disproportionate effluent 168, both of which are preferably unstabilized. The monofunctional reformate 126 and disproportionation effluent 168 may be fed to a stabilizer column 54. The overhead product 170 (the "hydrocarbon light ends") may be used as fuel gas. The bottoms product 172 (the "stabilized bottoms product") is fed to the B/T splitter 56. An overhead product 174 (the "first benzene-rich stream") is distilled overhead. The bottoms product 176 (the "first toluene-rich stream") is fed to the T/X splitter 60. The T/X splitter 60 separates the first toluene-rich stream 176 to provide a second toluene-rich stream 180 and a first xylene-rich stream 182.

Optionally, the monofunctional reformate 126 and the disproportionation effluent 168 combined and fed to the stabilizer column 54 at a single location. Preferably, the stabilizer column 54 has separate feed locations for the monofunctional reformate 126 and the disproportionation effluent 168, so that they may be distilled in a common distillation column but fed separately to the column based upon matching the feed with the internal composition profile inside the stabilizer column 54. Optionally, the feed to the disproportionation reactor is fed to the stabilizer tower 54.

K. Compressor/Chilled Water for Maximizing Benzene Recovery

Still another embodiment of the present invention for making high purity benzene and high purity paraxylene includes a process for recovering benzene from the monofunctional reformer produced light ends ("net gas"). This alternate embodiment comprises one or more of the following steps: (a) compressing the net gas from a monofunctional reformer and (b) partially condensing the net gas to recover benzene.

Among other factors, it has been discovered that the non-acidic catalyst used for the light reformer feed produces a large amount of benzene, the most volatile of the aromatics formed in the reformer, some of which remains in the net gas and is typically sent to a net gas recovery unit. On the other hand, where stabilizers rejecting a C4– hydrocarbon component are found, many C5– hydrocarbons are left to recycle in the aromatics complex reducing overall capacity. As such, it has been discovered that the recovery of benzene from the monofunctional reformer net gas may be significantly improved if chilled water, preferably from a lithium bromide chiller, is used to condense the benzene from the net gas stream. In addition, it has been discovered that the benzene recovery may be enhanced by combining the above discovery with that of limiting the stabilization of streams by processing an unstabilized isomerate. Optionally, the chilled water is used to separate benzene from the net gas following compression before entering the net gas recovery piping system. Optionally and preferably, the net gas from the aromatics unit is compressed in one or more stages with inter-stage cooling. The compressed net gas is then cooled using a lithium bromide chiller.

Figure 12:
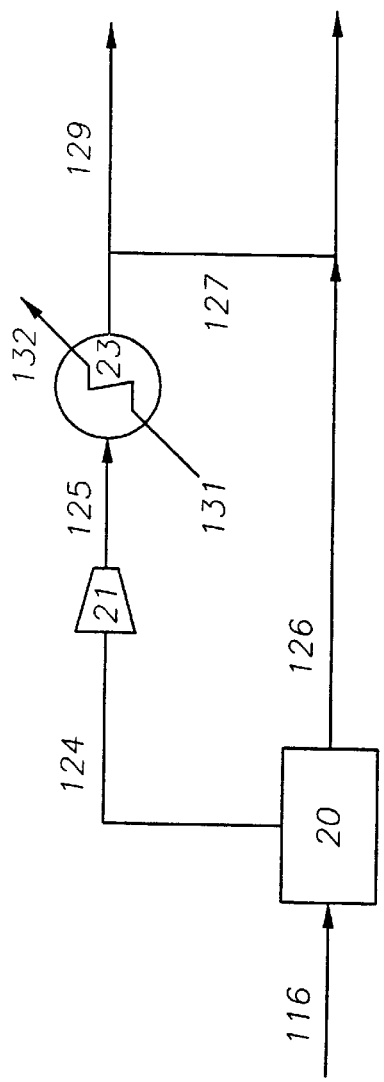
FIG. 12 is a block flow diagram of a specific embodiment of the invention illustrating the use of chilled water to maximize benzene recovery.

The partially condensed net gas is then fed to a separation drum where the condensed benzene is removed and combined with the light reformate. Referring to FIG. 12, a specific embodiment of the process of the present invention includes the compression of a net gas stream 124 from a monofunctional catalyst reformer 20 by a compressor 21 to provide a compressed net gas to be chilled in a shell and tube heat exchanger 23 by lithium bromide 131 to produce a liquefied benzene stream 127 to be combined with the monofunctional reformer reformate 126 ("light reformate") and a residue gas 129 for a net gas distribution system. Optionally, the net gas 124 from the monofunctional reformer 20 is compressed and chilled, preferably with an air cooler and a lithium bromide trim cooler, and then separated in a pressure vessel to provide a liquid aromatics stream comprising benzene to be combined with the light reformate 126. Preferably, the compression step 21 is a multi-stage compression with inter-stage coolers. Preferably, the inter-stage coolers are air coolers but optionally may be shell and tube exchangers with cooling water or other heat transfer liquid being used as the cooling media. Optionally and preferably, the net gas from the aromatics unit is compressed in one or more stages with inter-stage cooling with a pressure change A shell and tube heat exchanger, preferably using lithium bromide as the cooling media, chills the compressed net gas, in order to partially condense the net gas stream and recover liquid benzene. The liquid benzene is then separated from the partially condensed net gas stream in a pressure vessel. The recovered liquid benzene may then be combined with the light reformate 126. The residue net gas 129 may then be fed to a chlorine treater and then to the net gas distribution system.

Referring to FIG. 13, a specific embodiment of the process of the present invention will now be disclosed, as will preferred composition ranges for the various streams. The process in FIG. 13 includes fractionation of purchased naphtha 100 in a depentanizer 12 to provide an overhead gas product of C5– hydrocarbons for fuel gas 102. The bottoms product 104 is fractionated in the heavy naphtha distillation column 14 to separate heavy naphtha for storage 106 from the naphtha feed 108 which is sent to the naphtha hydrotreater 16. The hydrotreated naphtha 114 is fractionated in the naphtha splitter 18 to provide a light reformer feed 116 and a heavy reformer feed 118. The light reformer feed 116 is subjected to catalytic aromatization at elevated temperatures in the monofunctional catalyst reformer 20 in the presence of hydrogen and using a monofunctional, non-acidic catalyst comprising at least one Group VIII metal, preferably platinum, on a non-acidic zeolite L support to produce the first reformate stream 126. Optionally, liquid 128 recovered from any net gas recovery unit is combined and fed to the monofunctional catalyst reformer 20. The heavy reformer feed 118 is reformed in the bifunctional catalyst reformer 22 using a bifunctional catalyst comprising at least one Group VIII metal and a metallic oxide support, preferably a non-presulfided acidic catalyst comprising platinum and tin on an alumina support, to produce the second reformate stream 130. The second reformate is then stabilized by distillation in the heavy reformate stabilizer 24 to remove light gases 132 which are sent to the fuel gas system. The stabilized second reformate 134 is then clay-treated 26 to partially remove olefins. The first clay-treated stream 136 is then fractionated in the reformate splitter 28 to provide a light overhead product consisting of C7– hydrocarbons 140 and a C8+ hydrocarbon stream 138 ("the second xylene-rich stream") which is fed to the xylene rerun column 38. A third xylene-rich stream 194 is fractionated in the xylene rerun column 38 as overhead of the xylene rerun column 38 and is fed to the adsorber 40. The bottoms product from the xylene rerun column, e.g., the first gasoline stream 196, is fed to the heavy gasoline splitter 62 to recover C9 hydrocarbons in a heavy aromatic stream overhead 184 for recycle to the disproportionation step, preferably with transalkylation, and to produce a second gasoline product 186 which is sent to storage.

The adsorbent in the adsorber is a zeolitic adsorbent which exhibits a strong affinity or selectivity for paraxylene. Preferably, a Y zeolite is used, such as defined in U.S. Pat. No. 3,558,730 and in particular an exchange of both barium (45% to 65% of the sites) and potassium (35% to 55% of the sites). However, when the desorption solvent is p-diethyl benzene, the preferred zeolite is an X zeolite, also as defined in U.S. Pat. No. 3,558,730. In particular a quasi-total barium exchange with a residual sodium rate below 0.3% of the sites gives good results. In both cases, the zeolite is advantageously used in the form of balls with a grain size between 0.25 and 1 mm diameter and preferably between 0.35 and 0.8 mm diameter. In both cases, the water content o the zeolite is kept below 6% by weight and preferably below 3% by weight.

Preferably, the adsorber sequentially opens and closes different feed and product ports to simulate the movement of an adsorbent bed using fixed liquid inlet and outlet ports. More preferably, countercurrent adsorption is simulated. The adsorbed paraxylene-rich product stream 202 ("first paraxylene-rich stream") from the simulated moving bed is fed to an extract column 42. A side-stream product 204 (the "first internal recycle") is distilled in the extract column 42. The first internal recycle 204 is separated and recycled to the adsorber 40 from the paraxylene stream 206 ("second paraxylene-rich stream"). A light product stream 160 is taken overhead from the extract column 42 and recycled to a disproportionation reactor 52 to increase aromatic yields. The bottoms product 206 (the "second paraxylene-rich stream 206") is fed to crystallization unit 48. A raffinate product 200 from the adsorber 40 is fractionated in the raffinate column 44. A desorbent 198 (the "second internal recycle") is distilled overhead and recycled to the adsorber 40. A first paraxylene-deficient stream 208 is fed to an isomerization reactor 46. The isomerization reactor 46 produces an equilibrium distribution of xylene isomers formed from the first paraxylene-deficient stream 208 from the raffinate column 44. The isomerate 218 is fractionated in the light aromatics stabilizer column 50 to provide a fourth xylene-rich stream 220 for recycle to the xylene rerun column 38 following clay treatment 36 and a second benzene-rich stream 222 for recycle to a selective hydrogenation step 30 for benzene recovery.

The crystals produced in crystallization unit 48 are filtered, separated and washed in at least one separation and wash zone. A portion of the bottoms product 156 is sent to a clay treatment step 36 as make-up desorbent 150, while the remainder of the toluene-rich product 158 is fed to the disproportionation step 52. Preferably, the crystals are countercurrently washed, preferably with paraxylene, but other solvents such as toluene may be used. When washing with paraxylene, the resulting high purity paraxylene 214 should have a 99.9% by weight purity. The mother liquor 216 from the crystallization step 48 may be recycled to the xylene rerun column 38. The benzene stream 174 from the B/T splitter is combined with a second benzene-rich stream 222 and fed to a selective hydrogenation step 30 to produce a selective hydrogenation effluent 144 which is fed to the selective hydrogenation unit and extractive distillation unit. The selective hydrogenation step hydrogenates diolefins and partially hydrogenates olefins. The extract 152 from the selective dehydrogenation step is distilled in a benzene recovery column 34 to produce a high purity benzene product meeting or exceeding ASTM Refined Benzene-545 standard, discussed above.

The crystallization unit 48 preferably includes the components and configuration disclosed in copending application, U.S. Ser. No. 08/875,278. In accordance with the process shown therein, as applied to the present process, paraxylene is added to the xylene-rich stream that is fed to the crystallization unit, to form a paraxylene-enriched stream, which is subjected to a high temperature crystallization, preferably at a temperature between about +10 and −25° C., to form a suspension that includes paraxylene crystals, which are typically unwashed. Then, at least a portion of the crystals in the suspension are subjected to separation to separate them from the suspension. Next, at least a portion of the separated crystals are combined with paraxylene to form a slurry which is subjected to another separation to provide a liquid component that includes a paraxylene-rich liquid and a solids component that includes high purity paraxylene crystals, which is preferably the high purity paraxylene product that is one of the objectives of this invention. As discussed in the copending application, the separation of the slurry may be accomplished by washing of the separated crystals with a washing solvent. Alternatively, the separation of the slurry may be accomplished by subjecting the slurry to a centrifuge.

The disproportionation step uses an acidic para-selective catalyst, more preferably a para-selective catalyst which may be used to disproportionate the toluene into benzene and xylenes. Preferably, the disproportionation effluent 168 is subjected to a transalkylation in order to convert any C9 aromatics and toluene in the combined disproportionation feed stream 162 to produce benzene and xylenes. The combined disproportionation feed stream 162 includes a light product stream 160 taken is overhead from the extract column 42 and a heavy aromatic stream taken as overhead 184 from the heavy gasoline splitter 62. This disproportionation effluent 168 may then be combined with the first reformate stream 126. Optionally, both the disproportionation effluent 168 and the first reformate stream 126 are fed to separate locations in the stabilizer column 54 to remove any C5− hydrocarbons as light ends 170 which may be sent to fuel gas.

The stabilized bottoms product 172 is fed to the B/T splitter 56 where it is fractionated into a first benzene-rich stream 174. The B/T splitter bottoms product 176, i.e., the first xylene-rich stream, is clay-treated 58 to partially remove olefins. The clay treated effluent 178 is then distilled in a toluene/xylene splitter 60 ("T/X splitter") where it is fractionated into a second toluene-rich stream 180 which is recycled to the disproportionation reactor 52, and a first xylene-rich stream 182, which is recycled to the xylene rerun column 38.

Referring to FIG. 13, the compositions of the various streams may be varied, depending on the composition of the naphtha feedstock. Preferably, however, preferred "benchmark" compositions are used, particularly for purposes of adjusting the cut point in the naphtha feed splitter 18. Examples of such preferred benchmark compositions are as follows.

Referring again to FIG. 13, another specific embodiment of the process of the present invention includes the use of indirect heat exchange systems in the production of high purity benzene and high purity paraxylene. A specific embodiment of the process of the present invention may optionally, but preferably, include using a common distillation train for the monofunctional reformate 126 and the disproportionation effluent 168. These two streams may be mixed and fed to a single stabilizer column 54, or to individual feed trays within the stabilizer column 54. This specific embodiment of the invention includes five separate heat integrations such that overhead vapors from particular columns supply reboil duties to other distillation columns.

In particular, the monofunctional reformate stream 126 may be combined with the disproportionation effluent 168 to feed a stabilizer column 54. Optionally, but preferably, the two streams may be fed to separate feed trays within the stabilizer column 54. The first heat integration of the present invention occurs between the B/T splitter 56 and the T/X splitter 60. The stabilized bottoms product 172 from the stabilizer column 54 may be fed to a B/T splitter 56. A portion 256 of the splitter bottoms product 176 from the B/T splitter 56 may be used to condense a part of the overhead stream 180 (the second toluene-rich stream) from the T/X splitter 60. Following the heat exchange between the first reboiler stream 256 and the first condensing stream 260, the reboiled liquid 258 (the "first reboiled stream") is returned to the B/T splitter 56 and the condensed vapors 262 from the overhead of the T/X splitter 60 are returned to its associated reflux drum.

A second heat integration occurs between the heavy gasoline splitter 62 and the benzene recovery column 34. A portion 248 of the bottoms product 156 from the benzene recovery column 34 is withdrawn as stream 248 (the "second reboiler stream"). Stream 248 is used to condense a portion 252 of the overhead vapors from the heavy gasoline splitter 62 as stream 252 (the "second condensing stream). The second reboiled stream 250 is returned to the benzene recovery column 34. The second condensed stream 254 is returned to the heavy gasoline splitter 62.

A third heat integration occurs between the xylene rerun column 38 and the reformate splitter 28. A portion 224 of the bottoms product 138 (the second xylene-rich stream) from the reformate splitter 28 is used to condense a portion 228 of the overhead stream 194 (the third xylene-rich stream) from the xylene rerun column 38. The portion withdrawn from the bottoms product 138 to be reboiled, stream 224 (the "third reboiler stream"), indirectly contacts stream 228 (the "third condensing stream") to simultaneously reboil and condense the respective streams. The reboiled stream 226 (the "third reboiled stream") is returned to the reformate splitter 28 and the condensed vapors 230 (the "third condensed stream") are returned to the xylene rerun column 38.

A fourth heat integration occurs between the light aromatics stabilizer column 50 and the xylene rerun column 38. A portion 236 of the bottoms product 220 (the "fourth xylene-rich stream") is used to condense the portion of the overhead vapors from the xylene rerun column 38. The portion 236 of the bottoms product 220 to be reboiled 236 (the "fourth reboiler stream") is indirectly heat contacted with a portion 232 of the overhead vapors 194 from the xylene rerun column 38 as stream 232 (the "fourth condensing stream"). Following indirect heat contact, the reboiled liquid 238 (the "fourth reboiled stream") is returned to the light aromatics stabilizer column 50 and the condensed overhead vapors 234 (the "fourth condensed stream") are returned to the xylene rerun column 38.

A person skilled in the art will recognize many variations from the specific embodiments described above, based on information in this patent, without departing from the overall invention. Accordingly, the claims below are intended to cover any and all equivalents, including any changes or modifications of the invention which provide similar advantages and benefits and do not depart from the spirit of the invention.

What is claimed is:

1. A process for making high purity benzene and high purity paraxylene from a wide boiling point naphtha feed, comprising the steps of:
    (a) providing first and second naphtha fractions;
    (b) reforming the first and second naphtha fractions in the presence of first and second catalysts to provide first and second reformates, the first reformate being rich in benzene and toluene, the second reformate being rich in mixed xylenes;
    (c) subjecting the first reformate to a first distillation to separate benzene from toluene, and to provide a benzene-rich first reformate stream and a toluene-rich first reformate stream, and subjecting the toluene-rich first reformate stream to a second distillation to separate toluene from mixed xylenes in the toluene-rich first reformate stream;
    (d) subjecting the second reformate to a third distillation to remove benzene and to provide a benzene-deficient second reformate stream;
    (e) combining benzene removed from the third distillation of the second reformate of step (d) with the benzene-rich first reformate stream of step (c) to provide a combined benzene stream containing olefins and diolefins;
    (f) subjecting the combined benzene stream of step (e) to selective hydrogenation to hydrogenate at least some of the olefins and diolefins in the combined benzene stream and to provide a selectively hydrogenated benzene stream;
    (g) subjecting the selectively hydrogenated benzene stream to extractive distillation to provide a raffinate and an extract, removing the raffinate and treating the extract to distillation to provide light and heavy fractions, the light fraction being a high purity benzene; and
    (h) crystallizing the benzene-deficient second reformate stream of step (e) to convert a portion of the mixed xylenes in the benzene-deficient second reformate stream to paraxylene.

2. A process for making high purity benzene and high purity paraxylene from a wide boiling point naphtha feed, comprising the steps of:
    (a) separating the naphtha feed into a first reformer feed and a second reformer feed, the first reformer feed being rich in C7−'s, the second reformer feed being rich in C8+'s;
    (b) reforming the first and second reformer feeds separately in the presence of first and second catalysts to provide first and second reformates, wherein the first reformate is rich in benzene and toluene and the second reformate is rich in mixed xylenes, and wherein the second reformate has a higher concentration of mixed xylenes than the first reformate;
    (c) treating the first reformate to successive distillations by separating the first reformate into a first benzene-rich stream and a first toluene-rich stream, followed by separating the first toluene-rich stream into a second toluene-rich stream and a first xylene-rich stream, wherein the first xylene-rich stream has a higher concentration of mixed xylenes than the second toluene-rich stream;
    (d) distilling the second reformate to provide a second xylene-rich stream, wherein the second xylene-rich stream has a higher concentration of mixed xylenes than the second reformate;

(e) subjecting the second toluene-rich stream to disproportionation or transalkylation to provide a third xylene-rich stream comprising mixed xylenes;

(f) crystallizing the first and second xylene-rich streams separately, or combining the first and second xylene-rich streams to provide a combined xylene rich stream and crystallizing the combined xylene-rich stream, to provide one or more paraxylene-rich streams;

(g) purifying the one or more paraxylene-rich streams to provide a high purity paraxylene product.

3. A process for making high purity benzene and high purity paraxylene from a raw naphtha feedstock, comprising the steps of:

(a) removing from the raw feedstock a light end fraction comprising C5–'s and a heavy end fraction comprising C10+'s to provide a naphtha feed stream, wherein the raw feedstock contains C7's and the naphtha feed stream contains substantially all of the C7's contained in the raw feedstock;

(b) separating the naphtha feed stream into a C7– light fraction and a C8+ heavy fraction, wherein the C7– light fraction contains substantially all of the C7's contained in the raw feedstock and no more than about 10% C8+'s and the C8+ heavy fraction contains no more than about 10% C7–'s;

(c) reforming the C7– light fraction in the presence of a first catalyst to provide a light fraction reformate rich in benzene and toluene;

(d) reforming the C8+ heavy fraction in the presence of a second catalyst to provide a heavy fraction reformate rich in mixed xylenes, wherein the concentrations of benzene and toluene in the light fraction reformate are higher than the concentrations of benzene and toluene in the heavy fraction reformate;

(e) removing toluene and other aromatics from the light fraction reformate to provide a high purity benzene product; and (f) converting mixed xylene in the heavy fraction reformate to paraxylene and removing benzene and toluene from the heavy fraction reformate to provide a high purity paraxylene product.

4. A process for making high purity benzene and high purity paraxylene from a raw naphtha feedstock, comprising the steps of:

(a) splitting a naphtha feed stream into a first feed stream comprising a light fraction comprising C7–s and a second feed stream comprising a heavy fraction comprising C8+'s, said splitting being provided by distillation at a preselected first cut point;

(b) reforming the first feed stream in the presence of a first catalyst to provide a first reformate containing benzene and toluene and having a first preselected composition profile;

(c) reforming the second feed stream in the presence of a second catalyst to provide a second reformate containing mixed xylenes and having a second preselected composition profile; and (d) adjusting the preselected first cut point of step (a) in response to a benzene or paraxylene limit point to conduct the distillation of step (a) at a second cut point, wherein the benzene limit point corresponds to the concentration of benzene and toluene in the light fraction reformate, and the paraxylene limit point corresponds to the concentration of mixed xylenes in the heavy fraction reformate; wherein the preselected first cut point corresponds to the boiling point of a selected first component in the light fraction and the second cut point corresponds to the boiling point of a selected second component in the light fraction; and wherein the adjustment from the first cut point to the second cut point results in a change in the concentration of benzene and toluene in the light fraction reformate or a change in the concentration of mixed xylenes in the heavy fraction reformate.

5. The process of claim 4, wherein the limit point reflects a substantial change in the preselected composition profile of the first reformate.

6. The process of claim 4, wherein the first feed stream comprises C7–s and the cut point is adjusted to provide for more C7–'s in the second feed stream.

7. The process of claim 4, wherein the second feed stream comprises C8+s and the cut point is adjusted to provide for more C8+–'s in the first feed stream.

8. A process for making high purity benzene and high purity paraxylene from a raw naphtha feedstock, comprising the steps of:

(a) splitting a naphtha feed stream into a first feed stream comprising predominantly C7–'s and a second feed stream comprising predominantly C8+'s, said splitting being provided by distillation at a preselected cut point;

(b) reforming the first feed stream in the presence of a first catalyst to provide a first reformate having a preselected composition profile;

(c) reforming the second feed stream in the presence of a second catalyst to provide a second reformate having a preselected composition profile; and (d) adjusting the distillation cut point of step (a) in response to a substantial change in the preselected composition profile of the first reformate, wherein:

(e) the cut point is adjusted to provide for more C7–'s in the second feed stream in response to a substantial change in the composition profile of the first reformate; or (f) the cut point is adjusted to provide for more C8+–'s in the first feed stream in response to a substantial change in the composition profile of the second reformate.

9. A process for making high purity benzene and high purity paraxylene from a raw naphtha feedstock, comprising the steps of:

(a) separating a naphtha stream by distillation into a light fraction and a heavy fraction, said distillation being made at a preselected cut point, wherein the light fraction contains a first concentration of C7–'s and the heavy fraction contains a first concentration of C8+'s;

(b) reforming the light fraction in the presence of a first catalyst to provide a light fraction reformate that includes mixed aromatics;

(c) reaching a preselected limit point in the reforming of the light fraction, said limit point being based on the composition of the light fraction reformate;

(d) adjusting the preselected cut point after reaching said preselected limit point, to reduce the concentration of C7–'s in the light fraction and to increase the concentration of C7–'s in the heavy fraction.

10. A process for making high purity benzene and high purity paraxylene from a raw naphtha feedstock, comprising the steps of:

(a) removing a light end fraction and a heavy end fraction from the raw naphtha feedstock to provide a preconditioned naphtha feed stream, wherein the light end fraction comprises C5−'s and the heavy end fraction comprises C10+'s;

(b) separating the preconditioned naphtha feed stream by distillation at a predetermined cut point to provide a C7− light fraction and a C8+ heavy reformer fraction, wherein the C7− light fraction contains no more than about 10 wt % C8+'s and the C8+ heavy fraction contains no more than about 10 wt % C7−'s;

(c) reforming the C7− light fraction in the presence of a first catalyst to provide a first reformate stream comprising aromatics;

(d) reforming the C8+ heavy fraction in the presence of a second catalyst to provide a second reformate stream comprising aromatics;

(e) removing toluene and other aromatics from the first reformate stream to provide a high purity benzene product stream;

(f) removing at least a portion of the mixed xylenes from the second reformate stream and converting at least a portion of the removed mixed xylenes to paraxylene, to provide a high purity paraxylene product stream;

(g) identifying a predetermined benzene limit point in the reforming of step (c), the benzene limit point being a function of the composition of the first reformate stream;

(h) identifying a predetermined paraxylene limit point in the reforming of step (d), the paraxylene limit point being a function of the composition of the second reformate stream;

(i) adjusting the cut point of step (b) in response to either the benzene limit point in step (g) or the paraxylene limit point in step (h), wherein:

(j) the cut point is adjusted in response to the benzene limit point to provide a separation of the preconditioned naphtha feed stream such that the light fraction has fewer C7−'s and the heavy fraction has more C7−'s; and (k) the cut point is adjusted in response to the paraxylene limit point to provide a separation of the preconditioned naphtha feed stream such that the light fraction has more C8+'s and the heavy fraction has fewer C8+'s.

* * * * *